United States Patent
Charych et al.

(10) Patent No.: US 6,660,484 B2
(45) Date of Patent: Dec. 9, 2003

(54) COLORIMETRIC GLYCOPOLYTHIOPHENE BIOSENSORS

(75) Inventors: Deborah J. Charych, Albony, CA (US); Myung-Gi Baek, Ottawa (CA)

(73) Assignee: Regents of the University of California, Oakland, CA (US)

(*) Notice: Subject to any disclaimer, the term of this patent is extended or adjusted under 35 U.S.C. 154(b) by 0 days.

(21) Appl. No.: 09/734,410

(22) Filed: Dec. 11, 2000

(65) Prior Publication Data

US 2001/0026915 A1 Oct. 4, 2001

Related U.S. Application Data

(63) Continuation-in-part of application No. 09/461,509, filed on Dec. 14, 1999, now Pat. No. 6,395,561, which is a division of application No. 08/592,724, filed on Jan. 26, 1996, now Pat. No. 6,001,556, which is a continuation-in-part of application No. 08/159,927, filed on Nov. 30, 1993, now abandoned, which is a continuation-in-part of application No. 07/976,697, filed on Nov. 13, 1992, now abandoned, which is a continuation-in-part of application No. 09/500,295, filed on Feb. 8, 2000, which is a division of application No. 08/920,501, filed on Aug. 29, 1997, now Pat. No. 6,022,748, which is a continuation-in-part of application No. 09/103,344, filed on Jun. 23, 1998, and a continuation-in-part of application No. 08/609,312, filed on Mar. 1, 1996, now Pat. No. 6,183,772, which is a continuation-in-part of application No. 08/389,475, filed on Feb. 13, 1995, now abandoned, which is a continuation-in-part of application No. 08/289,384, filed on Aug. 11, 1994, now abandoned, and a continuation-in-part of application No. 08/328,237, filed on Oct. 24, 1994, now abandoned, which is a continuation-in-part of application No. 08/944,323, filed on Oct. 6, 1997, now Pat. No. 6,180,135, which is a division of application No. 08/389,475, which is a continuation-in-part of application No. 08/289,384, and a continuation-in-part of application No. 08/328,237, which is a continuation-in-part of application No. 09/023,898, filed on Feb. 13, 1998, which is a continuation-in-part of application No. 09/033,557, filed on Mar. 2, 1998, which is a continuation-in-part of application No. 09/337,973, filed on Jun. 21, 1999, now Pat. No. 6,306,598.

(60) Provisional application No. 60/170,190, filed on Dec. 10, 1999, provisional application No. 60/090,266, filed on Jun. 22, 1998, provisional application No. 60/050,496, filed on Jun. 23, 1997, provisional application No. 60/038,383, filed on Feb. 14, 1997, and provisional application No. 60/039,749, filed on Mar. 3, 1997.

(51) Int. Cl.[7] ................. G01N 33/53; G01N 33/566

(52) U.S. Cl. ............... 435/7.1; 435/5; 436/501; 436/528; 436/531; 436/527

(58) Field of Search .............. 435/5, 7.1; 436/501, 436/528, 531, 527

(56) References Cited

U.S. PATENT DOCUMENTS

| | | | | |
|---|---|---|---|---|
| 4,560,534 A | * | 12/1985 | Kung et al. .................. 422/68 |
| 4,818,677 A | * | 4/1989 | Hay-Kaufman et al. ....... 435/4 |
| 4,859,538 A | | 8/1989 | Ribi |
| 5,156,810 A | * | 10/1992 | Ribi ...................... 422/82.01 |
| 5,268,305 A | | 12/1993 | Ribi et al. |
| 5,283,333 A | * | 2/1994 | Bell .......................... 546/27 |
| 5,415,999 A | | 5/1995 | Saul et al. ................... 435/7.9 |
| 5,427,915 A | | 6/1995 | Ribi et al. |
| 5,480,582 A | | 1/1996 | Pope |
| 5,491,097 A | | 2/1996 | Ribi et al. |
| 5,521,101 A | | 2/1996 | Ribi et al. .................. 436/518 |
| 5,571,568 A | | 11/1996 | Ribi et al. |
| 5,618,735 A | | 4/1997 | Saul et al. .................. 428/518 |
| 5,622,872 A | | 4/1997 | Ribi |
| 6,001,556 A | | 12/1999 | Charych et al. ............... 435/5 |

OTHER PUBLICATIONS

Krämer, J. AOAC Intern. 79: 1245 [1996].
Gronow, *Trends Biochem. Sci.*, 9:336 [1984].
Finegold and Martin, Diagnostic Microbiology, 6th Ed. (1982), CV Mosby St. Louis pp. 13–15.
Roberts, *Langmuir–Blodgett Films*, Plenum, New York, [1990].
Skotheim, T. A., [ed.], "Handbook of Conducting Polymers," Marcel Dekker, New York [1986].
Bredas, J. L., and Silbey, R. [eds.], "Conjugated Polymers," Kluwer Acad. Publ., Dordrecht. [1990].
Frechette et al., "Monomer reactivity vs. Regioregularity in polythiophene derivatives," *Macromol. Chem. Phys.*, 198:1709–1722 [1990];.
Roncali, J., "Conjugated poly(yhiopheno): synthesis, functionalization, and applications," *Chem. Rev.*, 92:711–738 [1992].
Leclerc et al., "Chromic phenomena in neutral polythiophene derivatives," *Macromol. Chem. Phys.*, 197:2077–2087 [1996].
Roux et al., "Polythiophene derivatives: smart materials," *Polymer News*, 19:6–10 [1994].
Graf et al., "From monomers to $\pi$–stacks: A comprehensive study of the structure and properties of monomeric, $\pi$–dimerized, and $\pi$–stacked forms of the radical of 3',4'–dibutyl–2',5'–diphenyl–2,2':5', 2'–terthiophene," *J. Am. Chem. Soc.*, 119:5888–5899 [1997].
Patil et al., "Optical properties of conducting polymers," *Chem. Rev.*, 88:183–200 [1988].
Masella, M. J., and Swager, T. M., "Designing conducting polymer–based sensors: selective ionochromic response in crown ether containing polythiophenes," *J. Am. Chem. Soc.*, 115:12214–12215 [1993].
Crawford et al., "Na$^+$specific emission changes in an ionophoric conjugated polymer," *J. Am. Chem. Soc.*, 120:5187–5192 [1998].

(List continued on next page.)

*Primary Examiner*—James Housel
*Assistant Examiner*—Stacy S. Brown
(74) *Attorney, Agent, or Firm*—Hedlen & Carroll, LLP

(57) ABSTRACT

The present invention relates to methods and compositions for the direct detection of analytes using observable spectral changes in biopolymeric systems. In particular, the present invention allows for the direct colorimetric detection of analytes using color changes that occur in glycopolythiophene polymer systems in response to selective binding of analytes.

17 Claims, 13 Drawing Sheets

OTHER PUBLICATIONS

Faid, K., and Leclerc, M., "Functionalized regioregular polythiophenes: towards the development of biochromic sensors," *J. Chem. Soc., Chem. Commun.*, 2761–2762 [1996].

Pande et al., "A biotinylated undecylthiophene copolymer bioconjugate for surface immobilization: creating an alkaline phosphatase chemiluminescence–based biosensor," *Bioconjugate Chem.*, 7:159–164 [1996].

Charych et al., "Direct colorimetric detection of a receptor–ligand interaction by a polymerized bilayer assembly, " *Science*, 261:585–588 [1993].

Bredas, J. L., Relationship between band gap and bond length alternation in organic conjugated polymers, *J. Chem. Phys.*, 82:3809–3811 [1985].

Hernandez, V., "Confinement potential and π–electron delocalization in polyconjugated organic materials," *Phys. Rev. B 50*, 9815–9823 [1994].

Marsella et al., "Design of chemoresistive sensory materials: polythiophene–based pseudopolyrotaxanes," *J. Am. Chem. Soc.*, 117:9832–9841 [1995].

Bilewicz and Majda, Langmuir 7: 2794 [1991].

McCullough et al., "Self–assembly and disassembly of regioregular, water soluble polythiophenes: chemoselective ionchromatic sensing in water," *J. Am. Chem. Soc.*, 119:633–634 [1997].

Sharon, N., *"Complex Carbohydrates: Their Chemistry, Biosynthesis and Functions,"* Addison–Wesley, Reading, MA [1975].

Reutter et al., In *"Sialic acids, Chemistry, Metabolism, and Function, "* Cell biology monograph series, vol. 10, R. Schauer, [ed.], Springer–Verlag, Vienna [1982].

Goldstein, I. J., and Poretz, R. D., In *"The lectins. Properties, Functions and Applications in Biology and Medicine,"* Liener, I. E.; Sharon, N.; Goldstein, I. J. [eds.], Academic press, Orlando, Florida [1986].

Sharon, N., and Lis, H., "Carbohydrates in cell recognition," *Scientific American*, 82–89 [Jan. 1993].

Lee, Y. C., and Lee, Reiko T., *"Neoglycoconjugates: preparation and applications,"* Academic press [1994].

Toogood et al., "Monovalent sialosides that bind tightly to influenza A virus," *J. Med. Chem.*, 34:3138–3140 [1991].

Roy et al., "Synthetic oligosaccharides: indispensable probes for the life sciences," *ACS Symposium Series*, 560:104–119 [1993].

Klenk, H. D., and Rott, R., "The molecular biology of influenza virus pathogenicity," *Advances in Virus Research*, 34:247–281 [1988].

Orndorff, P. E., and Falkow, S., "Identification and characterization of a gene product that regulates type I pilation in Escherichia coli," *J. Bacterology*, 160:61–66 [1984].

Betozzi, C. R., and Bednarski, M. D., "A receptor–mediated immune response using synthetic glycoconjugates," *J. Am. Chem. Soc.*, 114:5543–5546 [1992].

Old, D. C., "Inhibition of the interaction between fimbrial haemagglutinins and erythrocytes by D–mannose and other carbohydrates," *J. Gen. Microb.*, 71:149–157 [1972].

Firon et al., "Carbohydrate–binding sites of the mannose–specific fimbrial lectins of enterobacteria," *Infection and Immunology*, 43:1088–1090 [1984].

Venegas et al., "Binding of type 1–piliated Escherichia coli to Vaginal mucus," *Infection and Immunology*, 63:416–422 [1995].

Madison et al., "Type I fimbrial shafts of Escherichia coli and klebsiella pneumoniae influence sugar–binding specificities of their fimH adhesins," *Infection and Immunology*, 62:843–848 [1994].

Roy et al., "Synthesis of esterase–resistant 9–O–acetylated polysialoside as inhibitor of influenza C virus hemagglutinin," *Angew. Chem. Int. Ed. Engl.*, 31:1478–1481 [1992].

Page et al., "Synthesis and lectin binding properties of dendritic mannopyranoside," *Chem. Commun.*, 1913–1914 [1996].

Hardman, K.D., "the carbohydrate binding site of concanavalin A," *ACS Symp. Ser.*, 88:12–26 [1979].

Lio et al., "Molecular imaging of thermochromic carbohydrate–modified polydiacetylene thin films," *Langmuir*, 13:6524 [1997].

McCullough, R. D., and Loewe, R. D., "Enhanced electrical conductivity in regioselectively synthesized poly(3–alkylthiophenes)," *J. Chem. Soc., Chem. Commun.*, 70–72 [1992].

McCullough et al., "Self–orienting head–to–tail poly(3–alkylthiophenes): new insights on structure–property relationships in conducting polymers," . *J. Am. Chem. Soc.*, 115:4910–4911 [1993].

Chen, T. A., and Rieke, R. D., "The first regioregular head–to–tail poly(3–hexylthiophene–2,5–diyl) and a regiorandom isopolymer: Ni vs. Pd catalyst of 2(5)–bromozincio–3–hexylthiophene polymerization," *J. Am. Chem. Soc. 114*, 10087–10088 [1992].

Leclerc et al., "Processing–induced chromism in thin films of polythiophene derivatives," *Macromol. Rapid Commun.*, 18:733–737 [1997].

Faid et al., "Chromic phenomena in regioregular and non-regioregular polythiophene derivatives," *Chem. Afater.*, 7:1390–1396 [1994].

Lee et al., "The effects of ester substitution and alkyl chain length on the properties of polythiophenes," *Synth. Met.*, 69:295–296 [1995].

Li et al., "A highly π–stacked organic semiconductor for thin film transistors based on fused thiophenes," *J. Am. Chem. Soc.*, 120:2206–2207 [1998].

Roux, C., and Leclerc, M., "Rod–totail transition in alkoxy–substituted polythiophenes," *Macromolecules*, 25:2141–2144 [1992].

Pincus, P., and De Gennes, P. G., "Nematic polymers," *J. Polym. Sci., Polym. Symp.*, 65:85–90 [1978].

Spaltenstein, A., and Whitesides, G., "Polyacrylamides bearing pendant α–sialoside groups strongly inhibit agglutination of erythrocytes by influenza virus," *J. Am. Chem. Soc.*, 113:686–687 [1991].

Rughooputh et al., "Chromism of soluble polythiophenes," *J. Polym. Sci., Part B: Polym. Phys.*, 25:1071–1078 [1987].

Gunther, G. R., "Concanavalin A derivatives with altered biological activities," *Proc. Nat. Acad. Sci.*, USA, 70:1012–1016 [1973].

Nagata, Y., and Burger, M. M., "Wheat germ agglutinin: molecular characteristics and specificity for sugar binding," *J. Biol. Chem.*, 249:3116–3122 [1974].

Yamamoto et al., "Extensive studies on π–stacking of poly(3–alkylthiophene–2,5–diyl)s and poly(4–alkylthiazole–2,5–diyl)s by optical spectroscopy, NMR analysis, light scattering analysis, and X–ray crystallography," *J. Am. Chem. Soc.*, 120:2047–2058 [1998].

Pagé, D., and Roy, R., "Synthesis of divalent π–D–mannopyranosylated clusters having enriched binding affinities towards concanavalin A and pea lectins," *Bioorg. Med. Chem. Lett.*, 6:7165–1770 [1996].
Wies et al., Nature 333: 426 [1988].
White et al., Cell 56: 725 [1989].
Wyrick et al., *Chlamydia* (Infect. Imm. 57: 2378 [1989].
Adish et al., Virology 176: 337 [1990].
Krah et al., Virology 172: 386 [1989].
Khatzman et al., Nature 312: 763 [1985].
Sacerdote et al., J. of Neuroscience Research 18: 102 [1987].
Ruff et al., FEBS Letters 211: 17 [1987].
Epstein et al., Nature 318: 663 [1985].
Lentz et al., Science 215: 182 [1982].
Carel et al., J. Biol. Chem. 265: 12293 [1990].
Marlin et al., Nature 344: 70 [1990].
Shephey et al., Proc. Natl. Acad. Sci. 85: 7743 [1988].
Mendelsohn et al., Cell 56: 855 [1989].
Kaner et al., Science 248: 1410 [1990].
Tronin et al., Langumuir 11: 385 [1995].
Vikholm et al., Langmuir 12: 3276 [1996].
Bamford et al., Adv. Mat. 6: 550 [1994].
Willner et al., Adv. Mat. 5: 912 [1993].
Downer et al., Biosensor and Bioelect. 7: 429 [1992].
Charych et al., Chem. and Biol. 3: 113 [1996].
Kosow et al., J. Biol. Chem. 246: 2618 [1971].
Bennett et al., Proc. Natl. Acad. Sci. 75: 4848 [1978].
Beswick and Pitt, J. Colloid Interface Sci. 124: 146 [1988].
Zhao and Reichert, Langmuir 8: 2785 [1992].
Furuki and Pu, Thin Solid Films 210: 471 [1992].
Kepley et al., Anal. Chem. 64: 3191 [1992].
Miyasaka et al., Chem. Lett. p. 627 [1990].
Co et al., Proc. Natl. Acad. Sci. 82: 1494 [1985].
Charych et al., "Specific Interaction of Influenza Virus with Organized Assemblies of Polydiacetylenes," *Mat. Res. Soc. Symp. Proc.* 282:153–161 (1993).
Yamanaka et al., "Solid Phase Immobilization of Optically Responsive Liposomes in Sol–gel Materials for Chemical and Biological Sensing," *Langmuir* 13:5049–5053 (1997).
Dagani, "Lipids and Minerals Form Novel Composite Microstructures," *Chem. & Eng. News*, 19–20 (1993).
Leung et al., "Imaging of polydiacetylene on graphite by scanning tunneling microscopy," *J. Appl. Phys.* 69(4):2044–2047 (1991).
Pons et al., "The Optical Activity and Circular Dichroic Spectra of Diacetylenic Phospholipid Polymers," *Biochim. Biophys. Acta* 693:461–465 (1982).
Berman et al., "Total Alignment of Calcite at Acidic Polydiacetylene Films: Cooperativity at the Organic–Inorganic Interface," *Science* 269:515–518 (1995).
Rieke et al., "Spatially Resolved Mineral Depositiion on Patterned Self–Assembled Monolayers," *Langmuir* 10:619–622 (1994).
Perez et al., "Toward Inorganic Monolayers Inserted in a Langmuir–Blodgett Matrix," *Thin Solid Films* 210/211:410–411 (1992).
Spevak, "The Presentation of Biological Ligands on the Surface of Polymerized Monolayers and Liposomes," Ph.D. Dissertation, University of California at Berkeley (1993).
Tanev and Pinnavaia, "Biomimetic Templating of Porous Lamellar Silicas by Vesicular Surfactant Assemblies," *Science* 271:1267–1269 (1996).

Kessel and Granick, "Formation and Characterization of a Highly Ordered and Well–Anchored Alkylsilane Monolayer on Mica by Self–Assembly," *Langmuir* 7:532–538 (1991).
Miyasaka et al., "Oriented Polypeptide Monolayers by Rapid Spontaneous Condensation of Amphiphilic Amino Acid Esters," *The Solid Films* 210/211:393–396 (1992).
Arisawa et al., "Quantitative characterization of enzymes adsorbed on to Langmuir–Blodgett films and the application to a urea sensor," *Thin Solid Films* 210:443–445 (1992).
Chance et al., "Thermal effects on the optical properties of single crystals and solution–cast films of urethane substituted polydiacetylenes," *J. Chem. Phys.* 71:206–211 (1979).
Kingery–Wood et al., "The Agglutination of Erythrocytes by Influenza Virus is Strongly Inhibited by Liposomes Incorporating an Analog of Sialyl Gangliosides," *J. Am. Chem. Soc.* 114:7303–7305 (1992).
Kaneko et al., "Absorption properties and structure changes caused by pre–annealing in polydiacetylene Langmuir–Blodgett films," *Thin Solid Films* 210:548–550 (1992).
Novotny et al., "Tribology of Langmuir–Blodgett Layers," *Langmuir* 5:485–489 (1989).
Okahata et al., "Preparations of Langmuir–Blodgett Films of Enzyme–Lipid Complexes: A Glucose Sensor Membrane," *Thin Solid Films* 180:65–72 (1989).
Ott et al., "Liposomes and influenza viruses as an in vitro model for membrane interactions II. Influence of vesicle size and preparation methods," *Eur. J. Pharm. Sci.* 6:333–341 (1994).
Reichert et al., "Polydiacetylene Liposomes Functionalized with Sialic Acid and Colorimetrically Detect Influenza Virus," *J. Am. Chem. Sci.* 117:829–830 (1995).
Shibata, "Reversible Colour Phase Transitions and Annealing Properties of Langmuir–Blodgett Polydiacetylene Films," *Thin Solid Films* 179:433–437 (1989).
Spevak et al., "Polymerized Liposomes Containing C–Glycosides of Sialic Acid: Potent Inhibitors of Influenza Virus in Vitro Infectivity," *J. Am. Chem. Soc.* 115: 1146–1147 [1993].
Swalen et al., "Molecular Monolayers and Films," *Langmuir* 3:932–950 (1987).
Tieke, "Langmuir–Blodgett Membranes for Separation and Sensing," *Adv. Mat.* 3:532–541 (1991).
Whitesides et al., "Wet Chemical Approaches to the Characterization of Organic Surfaces: Self–Assembled Monolayers, Wetting, and the Physical–Organic Chemistry of the Solid–Liquid Interface," *Langmuir* 6:87–96 (1990).
Lio et al., "Atomic force microscope study of chromatic transitions in polydiacetylene thin films," *J. Vac. Sci. Technol.* 14(2):1481–1486 (1996).
Mino et al., "Photoreactivity of 10,12–Pentacosadiynoic Acid Monolayers and Color Transitions of the Polymerized Monolayers on an Aqueous Subphase," *Langmuir* 8:594–598 (1992).
*Langmuir–Blodgett Films*; Wiley, New York (1996).
Day and Ringsdorf "Polymerization of Diacetylene Carbonic Acid Monolayers at the Gas–Water Interface," *J. Polym. Sci. Polym. Lett. Ed.* 16:205–210 (1978).
Roberts, *Langmuir–Blodgett Films*, Plenum, New York, [1990].
Roncali, J., "Conjugated poly(yhiopheno): synthesis, functionalization, and applications," *Chem. Rev.*, 92:711–738 [1992].
Roux et al., "Polythiophene derivatives: smart materials" *Polymer News*, 19:6–10 [1994].

Levesque, I., and Leclerc, M., "Ionochromic effects in regioregular ether–substituted polythiophenes," *J. Chem. Soc. Chem. Commun.*, 7:2293–2294 [1995].

Patil et al., "Optical properties of conducting polymers," *Chem. Rev.*, 88:183–200 [1988].

Hernandez, V., "Confinement potential and π–electron delocalization in polyconjugated organic materials," *Phys. Rev. B* 9815–9823 [1994].

McCullough et al., "Self–assembly and disassembly of regioregular, water soluble polythiophenes: chemoselective ionchromatic sensing in water," *J. Am. Chem. Soc.*, 119:633–634 [1997].

Reutter et al., In *"Sialic acids, Chemistry, Metabolism, and Function,"* Cell biology monography series, vol. 10, R. Schauer, [ed.], Springer–Verlag, Vienna [1982].

Goldstein, I. J., and Poretz, R. D., In *"The lectins. Properties, Functions and Applications in Biology and Medicine,"* Liener, I. E.; Sharon, N.; Goldstein, I. J. [eds.], Academic press, Orlando, Florida [1986].

Roy et al., "Synthetic oligosaccharides: indispensable probes for the life sciences," *ACS Symposium Series*, 560:104–119 [1993].

Klenk, H. D., and Rott, R., "The molecular biology of influenza virus pathogenicity," *Advances in Virus Research*, 34:247–281 [1988].

Faid et al., "Chromic phenomena in regioregular and non-regioregular polythiophene derivatives," *Chem. Afater.*, 7:1390–1396 [1994].

Pagé, D. and Roy, R., "Synthesis of divalent π–D–mannopyranosylated clusters having enriched binding affinities towards concanavalin A and pea lectins," *Bioorg. Med. Chem. Lett.*, 6:1765–1770 [1996].

Miyasaka et al., Chem. Lett., p. 627 [1990].

Lee et al., "The effects of ester substitution and alkyl chain length on the properties of polythiophenes," *Synth. Met.*, 69:295–296 [1995].

\* cited by examiner

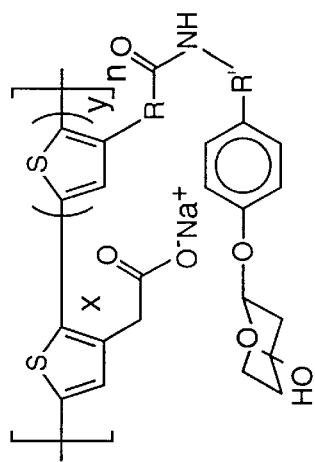

| R | R' | SIALIC ACID (%, W/W)[b] | MANNOSE (%, W/W)[b] |
|---|---|---|---|
| CH₂ | (CH₂)₃C(O)NH | 41 (48) | 49 (30) |
| CH₂ | (CH₂)₅C(O)NH | 42 (31) | 50 (48) |
| CH₂ | (CH₂)₂NHC(NH)(CH₂)₃S(CH₂)₂C(O)NH | 43 (50) | 51 (43) |
| CH₂ | (CH₂)₈NHC(NH)(CH₂)₃S(CH₂)₂C(O)NH | N/A[a] | 52 (28) |
| CH₂ | (CH₂)₂NHC(O)(CH₂)₂S(CH₂)₂NHC(NH)(CH₂)₃S(CH₂)₂C(O)NH | 44 (37) | 53 (31) |
| CH₂ | (CH₂)₂NHC(O)(CH₂)₂S(CH₂)₂NHC(NH)(CH₂)₃S(CH₂)₂C(O)NH | 45 (41) | N/A[a] |
| CH₂ | (CH₂)₅C(O)NH(CH₂)₂S(CH₂)₂C(O)NH | 46 (36) | N/A[a] |
| CH₂ | (CH₂)₈NHC(NH)(CH₂)₃S(CH₂)₂C(O)NH | 47 (49) | 54 (40) |
| CH=CH | | 48 (30) | 55 (32) |
| CH=CH | NHC(NH)(CH₂)₃S(CH₂)₂C(O)NH | | 56 (46) |

[a] NOT AVAILABLE. [b] WEIGHT PERCENT YIELDS OF POLYMERS.

FIG. 8

| POLYMER (SIALIC ACID) | $\lambda_{max}$(nm) (IN AQUEOUS) | $\lambda\Delta_{max}$(nm) | | |
|---|---|---|---|---|
| | | WGA | INFLUENZA A[a] | INFLUENZA B[a] |
| 40 | 440 | 0 | +4 | +3 |
| 41 | 408 | +1 | +6 | +15 |
| 42 | 429 | -4 | +5 | +6 |
| 43 | 429 | -2 | +10 | +10 |
| 44 | 401 | 0 | +15 | +15 |
| 45 | 415 | 0 | +27 | +32 |
| 46 | 416 | 0 | 0 | +3 |
| 47 | 411 | 0 | +4 | 0 |
| 48 | 422 | -6 | +14 | +17 |

[a] ASSAYS WERE PERFORMED AT 4° C.

FIG. 9

| POLYMER (MANNOSE) | $\lambda_{max}$(nm) (IN AQUEOUS) | $\lambda\Delta_{max}$(nm) | | |
|---|---|---|---|---|
| | | CON A[a] | C-B-S[b] | E. COLI (HB 101) |
| 40 | 440 | | +2 | +5 |
| 49 | 411 | | +5 | +16 |
| 50 | 405 | | +1 | +8 |
| 51 | 401 | | 0 | +18 |
| 52 | 410 | | +6 | +27 |
| 53 | 405 | | +4 | +21 |
| 54 | 405 | | +7 | +23 |
| 55 | 408 | | +8 | +25 |
| 56 | 415 | | +1 | +32 |

[a] PRECIPITATES WERE OBTAINED AFTER ADDITION OF CON A.
[b] C-B-S STANDS FOR CON A-BIOTIN-STREPTAVIDIN.

FIG. 10

COLORIMETRIC GLYCOPOLYTHIOPHENE BIOSENSORS

This application claims priority benefit of U.S. Provisional Application Serial No. 60/170,190 filed on Dec. 10, 1999. The present application is also a Continuation-in-Part Application of U.S. patent application Ser. No. 09/461,509, filed Dec. 14, 1999, now U.S. Pat. No. 6,395,561 which is a Divisional application of U.S. patent application Ser. No. 08/592,724, filed Jan. 26, 1996, now U.S. Pat. No. 6,001,556, issued Dec. 14, 1999, which is a Continuation-in-Part Application of U.S. patent application Ser. No. 08/159,927, filed Nov. 30, 1993, now abandoned, which is a Continuation-in-Part Application of U.S. patent application Ser. No. 07/976,697, filed Nov. 13, 1992, now abandoned. The present application is also a Continuation-in-Part Application of U.S. patent application Ser. No. 09/500,295, filed Feb. 8, 2000, which is a Divisional application of U.S. patent application Ser. No. 08/920,501, filed Aug. 29, 1997, now U.S. Pat. No. 6,022,748, issued Feb. 8, 2000. The present application is also a Continuation-in-Part Application of U.S. patent application Ser. No. 09/103,344, filed Jun. 23, 1998, which claims the benefit of U.S. Provisional Application No. 60/050,496, filed Jun. 23, 1997, and is also a Continuation-in-Part Application of U.S. patent application Ser. No. 08/609,312, filed Mar. 1, 1996, U.S. Pat. No. 6,183,772, which is a Continuation-in-Part Application of U.S. patent application Ser. No. 08/389,475, filed Feb. 13, 1995, now abandoned, which is a Continuation-in-Part Application of U.S. patent application Ser. No. 08/289,384, filed Aug. 11, 1994, now abandoned, and U.S. patent application Ser. No. 08/328,237, filed Oct. 24, 1994, now abandoned. The present application is also a Continuation-in-Part Application of U.S. patent application Ser. No. 08/944,323, filed Oct. 6, 1997, now U.S. Pat. No. 6,180,135, which is a Divisional application of U.S. patent application Ser. No. 08/389,475, listed above, which is a Continuation-in-Part Application of U.S. patent application Ser. No. 08/289,384, listed above, and U.S. patent application Ser. No. 08/328,237, listed above. The present application is also a Continuation-in-Part Application of U.S. patent application Ser. No. 09/023,898, filed Feb. 13, 1998, which claims priority to U.S. Provisional Application No. 60/038,383, filed Feb. 14, 1997. The present application is also a Continuation-in-Part Application of U.S. patent application Ser. No. 09/033,557, filed Mar. 2, 1998, which claims the benefit of U.S. Provisional Application No. 60/039,749, filed Mar. 3, 1997. The present application is also a Continuation-in-Part Application of U.S. patent application Ser. No. 09/337,973, filed Jun. 21, 1999, now U.S. Pat. No. 6,306,598, which claims the benefit of U.S. Provisional Application No. 60/090,266, filed Jun. 22, 1998.

FIELD OF THE INVENTION

The present invention relates to methods and compositions for the direct detection of analytes using observable spectral changes in biopolymeric systems. In particular, the present invention allows for the direct colorimetric detection of analytes using color changes that occur in glycopolythiophene polymer systems in response to selective binding of analytes.

BACKGROUND OF THE INVENTION

A major goal of analyte detection research is to develop inexpensive, fast, reliable, and sensitive detectors. Unfortunately, the technologies developed to date have only met some of these goals, and no single device has sufficiently attained a majority of them.

Classical detection methods such as liquid chromatography (LC), gas chromatography (GC), and supercritical fluid chromatography (SFC), in combination with mass spectrometry, are widely used and provide accurate identification of analytes and quantitative data. However, these techniques are time consuming, extremely expensive, require sample preconcentration, and are difficult or impossible to adapt to field use.

Biosensors (i.e., devices containing biological material linked to a transducing apparatus) have been developed to overcome some of the shortcomings of the classical analyte detection techniques. Many currently used biosensors are associated with transducer devices that use photometry, fluorimetry, and chemiluminescence; fiber optics and direct optical sensing (e.g., grating coupler); surface plasmon resonance; potentiometric and amperometric electrodes; field effect transistors; piezoelectric sensing; and surface acoustic wave (Krämer, J. AOAC Intern. 79: 1245 [1996]). However, there are major drawbacks to these devices, including their dependence on a transducing device, which prevents miniaturization and requires a power source. These disadvantages make such devices too complex, expensive, or unmanageable for many routine analyte detection applications such as field work or home use. Additionally, many of these devices are limited by the lack of stability and availability of the biological materials (e.g., proteins, antibodies, cells, and organelles).

The art remains in need of analyte detectors that provide the specificity of biosensors but also provide the cost-efficiency, stability, accuracy, reliability, reproducibility, and robustness that is lacking from available technologies. In particular, development of devices that can be miniaturized, that allow the detection of multiple analyte types, and that do not rely on an energy source would also be very beneficial, particularly for routine field work and home use.

SUMMARY OF THE INVENTION

The present invention relates to methods and compositions for the direct detection of analytes using observable spectral changes in biopolymeric systems. In particular, the present invention allows for the direct colorimetric detection of analytes using color changes that occur in glycopolythiophene polymer systems in response to selective binding of analytes.

The present invention provides biopolymeric materials comprising a plurality of polymerized monomers and one or more ligands, wherein the biopolymeric materials change color in the presence of analyte. In some embodiments, the ligands are selected from the group consisting of peptides, proteins, antibodies, receptors, channels, and combinations thereof, although the present invention contemplates all protein ligands (i.e., with protein being defined in its broadest sense). In other embodiments, the ligands are non-proteins (e.g., lectins, carbohydrates, glycolipids, phospholipids, and the like). However, the present invention is not limited to any particular ligand-analyte binding partners.

In particularly preferred embodiments, the biopolymeric materials comprise water-soluble glycopolythiophenes (e.g., containing sialic acid or mannose ligands) such materials have been synthesized by oxidative co-polymerization of methyl thiopheneacetate and thiophene-carbohydrate monomers.

In some embodiments, the inventive biopolymeric materials comprise three portions: a polymer, a spacer, and a ligand. Because of the adaptability of these assemblies, modifications may be made which give it great variety in application and design. The present invention is not limited to the following variations in some embodiments. Some preferred embodiments of the present invention employ variation in the polymer backbone, thereby producing different shapes of conjugation. This is accomplished through the addition of aromatic and or non-aromatic units (e.g., thiazole, pyrrole, selenophene phenyl unit, phenylene vinylene unit and diacetylene) as co-monomers without losing conjugation. Alternatively, the polymer backbone is altered by heterocyclic atoms used in place of carbon (e.g., N, O, and Se). Other embodiments of the present invention vary the length or composition of the spacer element. For example, almost any length spacer (e.g., one or more carbon atoms) having hydrophilic/lipophilic properties is permitted. The alteration of spacer length and composition is directed by observing the colorimetric responses obtained such that a desired response is reached. It is contemplated that the ability to vary spacer length and composition allows the polymer assemblies greater access to high molecular weight molecules (e.g., viruses, bacteria, and parasites). In preferred embodiments, neither the ligand, dopant, spacer, or polymer assembly comprises a lipid.

In still other embodiments, the ligand is varied according to the analyte to be detected. For example, in some embodiments, the ligand(s) employed include sugars, altered or naturally occurring polynucleotides (DNA, RNA, etc.), polypeptides, and other organic molecules capable of specifically binding to a receptor (e.g., cyclosporin, benzadiazapam, or serotonin uptake transporters, ACE), metal-complexes, and inorganic materials such as transition and lanthanide series metals.

It is not intended that the present invention be limited to one particular type of ligand molecule. A variety of ligand are contemplated. For example, the present invention provides for both protein and non-protein ligands. In some embodiments, protein ligands comprise antibodies or portions of antibodies, proteins, or polypeptides, and the like. In other embodiments that employ non-protein ligands, a number of non-protein molecules are contemplated (e.g., carbohydrates, nucleic acids, drugs, chromophores, antigens, chelating compounds, molecular recognition complexes, ionic groups, polymerizable groups, linker groups, electron donors, electron acceptor groups, hydrophobic groups, hydrophilic groups, receptor binding groups, polysacchrides (e.g., trisaccharides, tetrasaccharides, etc.) ganglioside $G_{M1}$, ganglioside $G_{T1b}$, sialic acid, and combinations thereof).

In alternative embodiments of the present invention, the portions of the ligand or monomer assemblies are manipulated to alter their shape and electronic conformation of the composition. For example, in some embodiments of the present invention, a carbohydrate ligand was placed next to the phenyl group of the glycopolythiophene assemblies to prevent neuraminidase cleavage of the O-linked glycosides of sialic acid and to provide tighter binding to *Escherichia coli.* Certain embodiments of the present invention were modified in this manner without losing binding properties.

Likewise, it is not intended that the present invention be limited to detecting any particular analyte. A variety of analytes are contemplated. In some embodiments, the analyte is selected from the group consisting of pathogens, drugs, receptor ligands, antigens, ions, hormones, blood components, disease indicators, cell components, antibodies, lectins, enzymes, organic solvents, volatile organic compounds, pollutants, and genetic material. Other embodiments are directed to pathogenic analytes, for example, viruses, bacteria, parasites, and fungi. In particular embodiments of the present invention, viral analytes are selected from the group consisting of influenza, rubella, varicella-zoster, hepatitis A, hepatitis B, herpes simplex, polio, small pox, human immunodeficiency virus, vaccinia, rabies, Epstein Barr, reoviruses, and rhinoviruses. However, it is understood that many other viruses or portions of viruses may be selected as suitable analytes. In still other embodiments, pathogenic analytes comprise bacterium, or portions of bacterium (e.g., *E. coli, Mycobacterium tuberculosis,* Salmonella, Chlamydia and Streptococcus). Alternative embodiments are directed to parasitic analytes (e.g., Plasmodium, Trypanosoma, *Toxoplasma gondii,* and Onchocerca) or portions of these parasites.

Still further embodiments of the present invention employ accessory molecules (i.e., dopants) that alter ligand-receptor binding. As used herein "alter ligand binding" encompasses both attenuating or enhancing ligand binding (the colorimetric response of the polymer assemblies upon the binding of an analyte may, or may not, be effected by the particular dopant selected). The present invention also contemplates a number of means, both covalent and noncovalent, for attaching these dopant molecules. For example, in some embodiments, these molecules are attached directly to the polymer assemblies, alternatively, these molecules are attached to the polymer assemblies via a linker. In still other embodiments, these molecules are attached to the ligand or receptor molecules themselves. In any event, the molecules are positioned relative to the polymer assemblies such that a desired effect is exerted on ligand binding or colorimetric response. Other embodiments of the present invention employ alternative physical schemes for altering ligand binding and colorimetric response (e.g., heat, pressure, irradiation, and the like).

In some embodiments of the present invention, the dopant material comprises surfactants, polysorbate, octoxynol, sodium dodecyl sulfate, polyethylene glycol, zwitterionic detergents, decylglucoside, deoxycholate, diacetylene derivatives, phosphatidylserine, phosphatidylinositol, phosphatidylethanolamine, phosphatidylcholine, phosphatidylglycerol, phosphatidic acid, phosphatidylmethanol, cardiolipin, ceramide, cholesterol, steroids, cerebroside, lysophosphatidylcholine, D-erythroshingosine, sphingomyelin, dodecyl phosphocholine, and N-biotinyl phosphatidylethanolamine.

In particularly preferred embodiments of the present invention, the biopolymeric materials are designed to produce freely soluble polymers in aqueous solution and to increase inter-chain interactions so that the compositions (e.g., glycopolythiophenes, polythiophenes, and thiophenes) are more sensitive to external stimuli. This unique feature distinguishes this invention from other polymers. However, the present invention is not intended to be limited to any particular configuration. Various configurations are envisioned. In one embodiment, the polymer assemblies comprise linear glycopolymers. In other embodiments, the polymer assemblies are configured as films, or vesicles. Still further embodiments contemplate compositions and methods employing immubolized polymers (e.g., various substrates, including microtitter plates, tubes, and wells).

The present invention is not intended to be limited to any particular method of polymer assembly or synthesis. Indeed, a number of polymer assembly synthesis techniques are contemplated. For example, in some embodiments, the polymer assemblies are synthesized by oxidative polymerization by the described $FeCl_3$ method. In alternative embodiments, the polymer assemblies are synthesized via graft conjugation of carbohydrates by the described peptide coupling method.

It is not intended that the present invention be limited to glycopolythiphene monomers. A variety of polymerizable monomers are contemplated. In one embodiment, thiophene monomers are used. In another embodiment, polythiophene monomers are used.

In some particularly preferred embodiments of the present invention, the compositions further comprise one or more spacer molecules. Suitable spacer molecules can be hydrophilic or hydrophobic. In some of these embodiments, the spacer molecule comprise from 1–1,000 carbon atoms, preferably from 100–500 carbon atoms, more preferably from 20–50 carbon atoms, and most preferably from 5–10 carbon atoms. Additionally, in some embodiments, one or more covalent bonds attach one or more ligands to the biopolymeric materials (e.g., amine bonds, sulfide bonds, thiol bonds, aldehyde bonds, glycosidic bonds, and peptide bonds). In some of these embodiments, also comprise one or more spacer molecules.

In preferred embodiments of the present invention, a colorimetric response is obtained from conformational changes in the biopolymeric assemblies. While an understanding of the mechanism is not important to practice of the present invention, the colorimetric response is believed to result from stress induced in the polymer through the binding of an attached ligand and its analyte.

The present invention also provides methods of detecting the presence of an analyte in a sample, comprising: a) providing: i) biopolymeric materials comprising a plurality of monomers and one or more ligands wherein said biopolymeric materials change color in the presence of an analyte; and ii) a sample suspected of containing an analyte; a) contacting said biopolymeric materials with said sample; and b) detecting a color change in said biopolymeric materials. Indeed, the present invention contemplates various methods and kit embodiments for detecting the presence of analytes using the novel colorimetric biopolymeric materials disclosed herein. For example, the compositions and methods of the presention are readily suited for assays employed to discover various reaction inhibitors. Moreover, the compositions and methods of the present invention are fully scale-able for uses requiring high throuphput screening techniques such as drug development, analytical chemistry, genomics, and proteomics.

The present inventive assemblies can also be applied to the manufacture of environmental biosensors for the detection of air and water contaminants and contaminants in food and beverages. In still further embodiments, the inventive compositions are incorporated with surgical instruments or medical consumables (e.g, bandages and wound dressings, catheters, etc.) such that clinicians and other helathcare workers can moniter the presence of an analyte (e.g., a bacterial toxin, or metabolite). In still further embodiments, the compositions and methods of the present invention are devised for the home health care nmarkets (e.g., pregnancy tests, glucose and insulin level monitoring).

DESCRIPTION OF THE FIGURES

FIG. 8 shows various monomers prepared by the oxidative polymerization with $FeCl_3$ method (compounds 41–56).

FIG. 9 shows UV-Vis spectroscopic data of reactions of Series I sialic acid-PTs (compounds 40–48) with receptor proteins.

FIG. 10 shows UV-Vis spectroscopic data of reactions of Series II mannose-PTs (compounds 40, and 49–56) with receptor proteins.

DEFINITIONS

Figure 1:
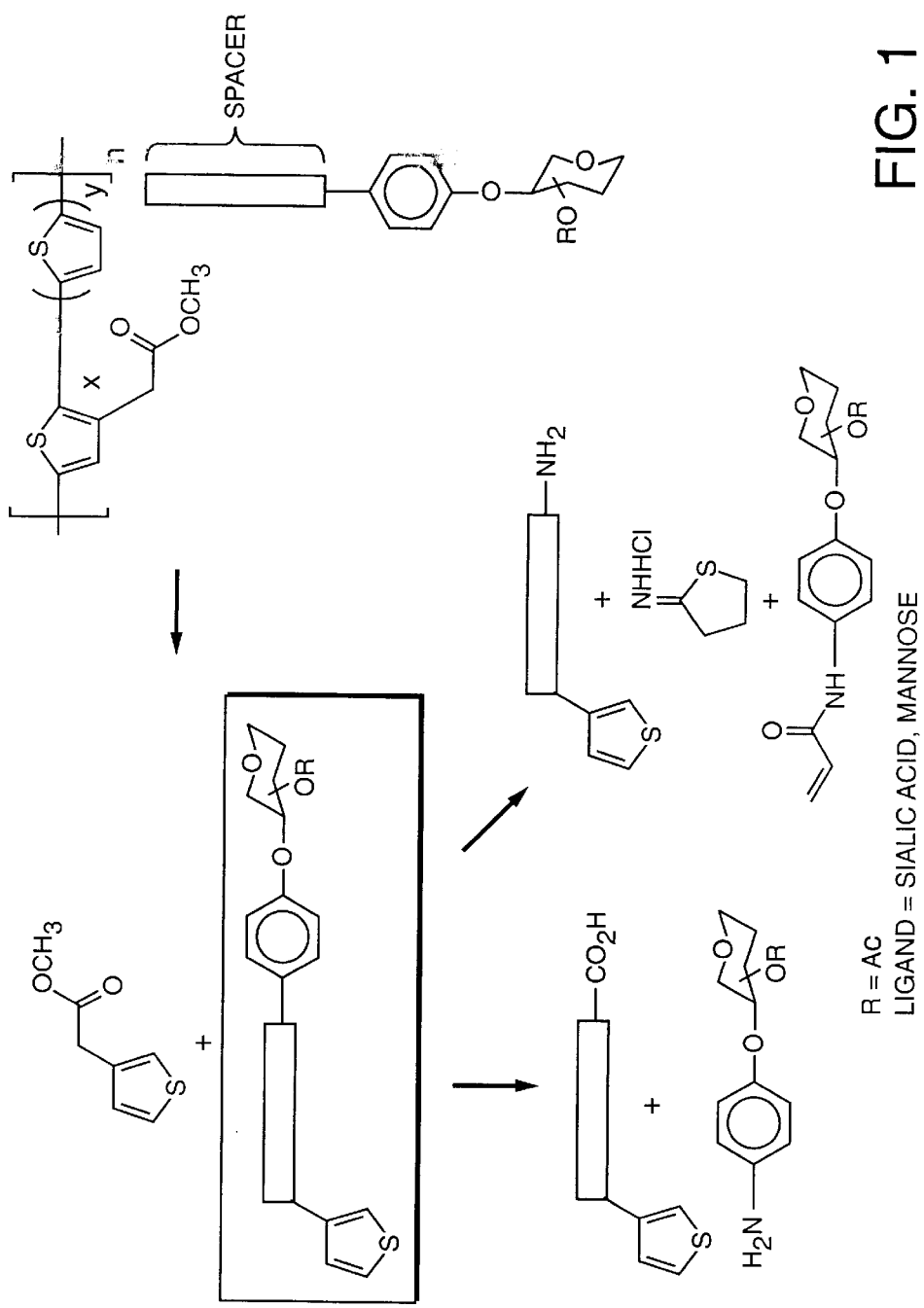
FIG. 1 shows a retrosynthetic analysis of various glyco-polythiophenes compositions.

To facilitate an understanding of the present invention, a number of terms and phrases are defined below:

As used herein, the term "immobilization" refers to the attachment or entrapment, either chemically or otherwise, of material to another entity (e.g., a solid support) in a manner that restricts the movement of the material.

As used herein, the terms "material" and "materials" refer to, in their broadest sense, any composition of matter.

As used herein, the term "biopolymeric material" refers to materials composed of polymerized biological molecules (e.g., lipids, proteins, carbohydrates, and combinations thereof). Such materials include, but are not limited to, films, vesicles, liposomes, multilayers, aggregates, membranes, and solvated polymers (e.g., polythiophene aggregates such as rods and coils in solvent). Biopolymeric material can contain molecules that are not part of the polymerized matrix (i.e., molecules that are not polymerized).

As used herein the term "protein" is used in its broadest sense to refer to all molecules or molecular assemblies containing two or more amino acids. Such molecules include, but are not limited to, proteins, peptides, enzymes, antibodies, receptors, lipoproteins, glycoproteins, and channels.

As used herein the term "antibody" refers to a glycoprotein evoked in an animal by an immunogen (antigen). An antibody demonstrates specificity to the immunogen, or, more specifically, to one or more epitopes contained in the immunogen. Native antibody comprises at least two light polypeptide chains and at least two heavy polypeptide chains. Each of the heavy and light polypeptide chains contains at the amino terminal portion of the polypeptide chain a variable region (i.e., VH and VL respectively), which contains a binding domain that interacts with antigen. Each of the heavy and light polypeptide chains also comprises a constant region of the polypeptide chains (generally the carboxy terminal portion) which may mediate the binding of the immunoglobulin to host tissues or factors influencing various cells of the immune system, some phagocytic cells and the first component (C1q) of the classical complement system. The constant region of the light chains is referred to as the "CL region," and the constant region of the heavy chain is referred to as the "CH region." The constant region of the heavy chain comprises a CH1 region, a CH2 region, and a CH3 region. A portion of the heavy chain between the CH1 and CH2 regions is referred to as the hinge region (i.e., the "H region"). The constant region of the heavy chain of the cell surface form of an antibody further comprises a spacer-transmembranal region (M1) and a cytoplasmic region (M2) of the membrane carboxy terminus. The secreted form of an antibody generally lacks the M1 and M2 regions.

As used herein, the term "biopolymeric films" refers to polymerized organic films that are used in a thin section or in a layer form. Such films can include, but are not limited to, monolayers and bilayers. Biopolymeric films can mimic biological cell membranes (e.g., in their ability to interact with other molecules such as proteins or analytes).

As used herein, the term "direct colorimetric detection" refers to the detection of color changes without the aid of an intervening processing step (e.g., conversion of a color change into an electronic signal that is processed by an interpreting device). It is intended that the term encompass visual observing (e.g., observing with the human eye).

As used herein, the term "analytes" refers to any material that is to be analyzed. Such materials can include, but are not limited to, molecules, bacteria, compounds, viruses, cells, antibodies, and cell parts.

As used herein, the term "selective binding" refers to the binding of one material to another in a manner dependent upon the presence of a particular molecular structure (i.e., specific binding). For example, a receptor will selectively bind ligands that contain the chemical structures complementary to the ligand binding site(s).

As used herein, the term "biosensors" refers to any sensor device that is partially or entirely composed of biological molecules. In a traditional sense, the term refers to "an analytical tool or system consisting of an immobilized biological material (such as enzyme, antibody, whole cell, organelle, or combination thereof) in intimate contact with a suitable transducer device which will convert the biochemical signal into a quantifiable electrical signal" (Gronow, *Trends Biochem. Sci.,* 9:336 [1984]).

As used herein, the term "transducer device" refers to a device that is capable of converting a non-electrical phenomenon into electrical information, and transmitting the information to a device that interprets the electrical signal. Such devices can include, but are not limited to, devices that use photometry, fluorimetry, and chemiluminescence; fiber optics and direct optical sensing (e.g., grating coupler); surface plasmon resonance; potentiometric and amperometric electrodes; field effect transistors; piezoelectric sensing; and surface acoustic wave.

As used herein, the term "miniaturization" refers to a reduction in size, such as the size of a sample to increase utility (e.g., portability, ease of handling, and ease of incorporation into arrays).

As used herein, the term "stability" refers to the ability of a material to withstand deterioration or displacement and to provide reliability and dependability.

As used herein, the term "conformational change" refers to the alteration of the molecular structure of a substance. It is intended that the term encompass the alteration of the structure of a single molecule or molecular aggregate (e.g., the change in structure of polythiophenes or glycopolythiophenes upon interaction with an analyte).

As used herein, the term "small molecules" refers to any molecule with low molecular weight (i.e., less than 10,000 atomic mass units and preferably less than 5,000 atomic mass units) that binds to ligands, interacts with ligands, or interacts with biopolymeric material in a manner that creates a conformational change.

As used herein, the term "pathogen" refers to disease causing organisms, microorganisms, or agents including, but not limited to, viruses, bacteria, parasites (including, but not limited to, organisms within the phyla Protozoa, Platyhelminthes, Aschelminthes, Acanthocephala, and Arthropoda), fungi, and prions.

As used herein, the term "bacteria" and "bacterium" refer to all prokaryotic organisms, including those within all of the phyla in the Kingdom Procaryotae. It is intended that the term encompass all microorganisms considered to be bacteria including Mycoplasma, Chlamydia, Actinomyces, Streptomyces, and Rickettsia. All forms of bacteria are included within this definition including cocci, bacilli, spirochetes, spheroplasts, protoplasts, etc. "Gram negative" and "gram positive" refer to staining patterns obtained with the Gram-staining process which is well known in the art (See e.g., Finegold and Martin, Diagnostic Microbiology, 6th Ed. (1982), C V Mosby St. Louis, pp 13–15).

As used herein, the term "membrane" refers to, in its broadest sense, a thin sheet or layer of material. It is intended that the term encompass all "biomembranes" (i.e., any organic membrane including, but not limited to, plasma membranes, nuclear membranes, organelle membranes, and synthetic membranes). Typically, membranes are composed of lipids, proteins, glycolipids, steroids, sterols and/or other components. As used herein, the term "membrane fragment" refers to any portion or piece of a membrane. The term "polymerized membrane" refers to membranes that have undergone partial or complete polymerization.

As used herein, the term "polymerization" encompasses any process that results in the conversion of small molecular monomers into larger lecules consisting of repeated units. Typically, polymerization involves chemical crosslinking of monomers to one another.

As used herein, the term "membrane receptors" refers to constituents of membranes that are capable of interacting with other molecules or materials. Such constituents can include, but are not limited to, proteins, lipids, carbohydrates, and combinations thereof.

As used herein, the term "volatile organic compound" or "VOC" refers to organic compounds that are reactive (i.e., evaporate quickly, explosive, corrosive, etc.), and typically are hazardous to human health or the environment above certain concentrations. Examples of VOCs include, but are not limited to, alcohols, benzenes, toluenes, chloroforms, and cyclohexanes.

As used herein, the term "enzyme" refers to molecules or molecule aggregates that are responsible for catalyzing chemical and biological reactions. Such molecules are typically proteins, but can also comprise short peptides, RNAs, or other molecules.

As used herein, the term "drug" refers to a substance or substances that are used to diagnose, treat, or prevent diseases or conditions. Drugs act by altering the physiology of a living organism, tissue, cell, or in vitro system that they are exposed to. It is intended that the term encompass antimicrobials, including, but not limited to, antibacterial, antifungal, and antiviral compounds. It is also intended that the term encompass antibiotics, including naturally occurring, synthetic, and compounds produced by recombinant DNA technology.

As used herein, the term "peptide" refers to any substance composed of two or more amino acids.

As used herein, the term "carbohydrate" refers to a class of molecules including, but not limited to, sugars, starches, cellulose, chitin, glycogen, and similar structures. Carbohydrates can also exist as components of glycolipids and glycoproteins.

As used herein, the term "chromophore" refers to molecules or molecular groups responsible for the color of a compound, material, or sample.

As used herein, the term "antigen" refers to any molecule or molecular group that is recognized by at least one antibody. By definition, an antigen must contain at least one epitope (i.e., the specific biochemical unit capable of being recognized by the antibody). The term "immunogen" refers to any molecule, compound, or aggregate that induces the production of antibodies. By definition, an immunogen must contain at least one epitope (i.e., the specific biochemical unit capable of causing an immune response).

As used herein, the term "chelating compound" refers to any compound composed of or containing coordinate links that complete a closed ring structure.

As used herein, the term "molecular recognition complex" refers to any molecule, molecular group, or molecular complex that is capable of recognizing (i.e., specifically interacting with) a molecule.

As used herein, the term "ambient condition" refers to the conditions of the surrounding environment (e.g., the temperature of the room or outdoor environment in which an experiment occurs).

As used herein, the term "room temperature" refers, technically, to temperatures approximately between 20 and 25 degrees centigrade. However, as used generally, it refers to the any ambient temperature within a general area in which an experiment is taking place.

As used herein, the terms "home testing" and "point of care testing" refer to testing that occurs outside of a laboratory environment. Such testing can occur indoors or outdoors at, for example, a private residence, a place of business, public or private land, in a vehicle, under water, as well as at the patient's bedside.

As used herein, the term "lipid" refers to a variety of compounds that are characterized by their solubility in organic solvents. Such compounds include, but are not limited to, fats, waxes, steroids, sterols, glycolipids, glycosphingolipids (including gangliosides), phospholipids, terpenes, fat-soluble vitamins, prostaglandins, carotenes, and chlorophylls. As used herein, the phrase "lipid-based materials" refers to any material that contains lipids.

As used herein, the term "lipid cleavage" refers to any reaction that results in the division of a lipid or lipid-comprising material into two or more portions. "Lipid cleavage means" refers to any means of initiating and/or catalyzing lipid cleavage. Such lipid cleavage means include, but are not limited to enzymes, free radical reactions, and temperature changes.

As used herein, the term "lipase" refers to any of a group of hydrolytic enzymes that acts on ester bonds in lipids. Such lipases include, but are not limited to, pancreatic lipase that catalyses the hydrolysis of triacylglycerols, lipoprotein lipase that catalyzes the hydrolysis of triacylglycerols to glycerol and free fatty acids, and phospholipases, among others. The term "phospholipase" refers to enzymes that cleave phospholipids by the hydrolysis of carbon-oxygen or phosphorus-oxygen bonds. Phospholipases include, but are not limited to, phospholipases $A_1$, $A_2$, C, and D.

As used herein, the term "enzyme" refers to any molecule, or aggregation of molecules, that accelerates or catalyzes a chemical reaction.

As used herein, the term "virus" refers to minute infectious agents, which with certain exceptions, are not observable by light microscopy, lack independent metabolism, and are able to replicate only within a living host cell. The individual particles (i.e., virions) consist of nucleic acid and a protein shell or coat; some virions also have a lipid containing membrane. The term "virus" encompasses all types of viruses, including animal, plant, phage, and other viruses.

As used herein, the phrase "free floating aggregates" refers to aggregates that are not immobilized.

As used herein, the term "encapsulate" refers to the process of encompassing, encasing, or otherwise associating two or more materials such that the encapsulated material is immobilized within or onto the encapsulating material.

As used herein, the term "optical transparency" refers to the property of matter whereby the matter is capable of transmitting light such that the light can be observed by visual light detectors (e.g., eyes and detection equipment).

As used herein, the term "biologically inert" refers to a property of material whereby the material does not chemically react with biological material.

As used herein, the term "organic solvents" refers to any organic molecules capable of dissolving another substance. Examples include, but are not limited to, chloroform, alcohols, phenols, and ethers.

As used herein, term "nanostructures" refers to microscopic structures, typically measured on a nanometer scale. Such structures include various three-dimensional assemblies, including, but not limited to, liposomes, films, multilayers, braided, lamellar, helical, tubular, and fiber-like shapes, and combinations thereof. Such structures can, in some embodiments, exist as solvated polymers in aggregate forms such as rods and coils.

As used herein, the term "films" refers to any material deposited or used in a thin section or in a layer form.

As used herein, the term "vesicle" refers to a small enclosed structures. Often the structures are membranes composed of lipids, proteins, glycolipids, steroids or other components associated with membranes. Vesicles can be naturally generated (e.g., the vesicles present in the cytoplasm of cells that transport molecules and partition specific cellular functions) or can be synthetic (e.g., liposomes).

As used herein, the term "liposome" refers to artificially produced spherical lipid complexes that can be induced to segregate out of aqueous media.

As used herein, the term "biopolymeric liposomes" refers to liposomes that are composed entirely, or in part, of biopolymeric material.

As used herein, the term "tubules" refers to materials comprising small hollow cylindrical structures.

As used the term "multilayer" refers to structures comprised of two or more monolayers. The individual monolayers may chemically interact with one another (e.g., through covalent bonding, ionic interactions, van der Waals' interactions, hydrogen bonding, hydrophobic or hydrophilic assembly, and stearic hindrance) to produce a film with novel properties (i.e., properties that are different from those of the monolayers alone).

As used herein, the terms "self-assembling monomers" and "lipid monomers" refer to molecules that spontaneously associate to form molecular assemblies. In one sense, this can refer to surfactant molecules that associate to form surfactant molecular assemblies. "Surfactant molecular assemblies" refers to an assembly of surface active agents that contain chemical groups with opposite polarity, form oriented monolayers at phase interfaces, form micelles (colloidal particles in aggregation colloids), and have detergent, foaming, wetting, emulsifying, and dispersing properties.

As used herein, the term "homopolymers" refers to materials comprised of a single type of polymerized molecular species. The phrase "mixed polymers" refers to materials comprised of two or more types of polymerize molecular species.

As used herein, the term "ligands" refers to any ion, molecule, molecular group, or other substance that binds to another entity to form a larger complex. Examples of ligands include, but are not limited to, peptides, carbohydrates, nucleic acids, antibodies, or any molecules that bind to receptors. The term "non-protein ligands" refers to all such ligands with the exception of proteins (defined above).

As used herein, the terms "organic matrix" and "biological matrix" refer to collections of organic molecules that are assembled into a larger multi-molecular structure. Such structures can include, but are not limited to, films, monolayers, and bilayers. As used herein, the term "organic monolayer" refers to a thin film comprised of a single layer of carbon-based molecules. In one embodiment, such monolayers can be comprised of polar molecules whereby the hydrophobic ends all line up at one side of the monolayer. The term "monolayer assemblies" refers to structures comprised of monolayers. The term "organic polymetric matrix" refers to organic matrices whereby some or all of the molecular constituents of the matrix are polymerized.

As used herein, the phrase "head group functionality" refers to the molecular groups present an the ends of molecules (e.g., the carboxylic acid group at the end of fatty acids).

As used herein, the term "hydrophilic head-group" refers to ends of molecules that are substantially attracted to water by chemical interactions including, but not limited to, hydrogen-bonding, van der Waals' forces, ionic interactions, or covalent bonds. As used herein, the term "hydrophobic head-group" refers to ends of molecules that self-associate with other hydrophobic entities, resulting in their exclusion from water.

As used herein, the term "carboxylic acid head groups" refers to organic compounds containing one or more carboxyl (—COOH) groups located at, or near, the end of a molecule. The term carboxylic acid includes carboxyl groups that are either free or exist as salts or esters.

As used herein, the term "detecting head group" refers to the molecular group contained at the end of a molecule that is involved in detecting a moiety (e.g., an analyte).

As used herein, the term "linker" or "spacer molecule" refers to material that links one entity to another. In one sense, a molecule or molecular group can be a linker that is covalent attached two or more other molecules (e.g., linking a ligand or receptor to a monomer).

As used herein, the phrase "polymeric assembly surface" refers to polymeric material that provides a surface for the assembly of further material (e.g., a biopolymeric surface of a film, liposome, or polymer that provides a surface for attachment and assembly of ligands).

As used herein, the phrase "chromatic detection element" refers to material that is capable of providing colorimetric analysis (e.g., polymerized polythiophene, or glycopolythiophene).

As used herein, the term "formation support" refers to any device or structure that provides a physical support for the production of material. In some embodiments, the formation support provides a structure for layering and/or compressing films.

As used herein, the terms "standard trough" and "standard Langmuir-Blodgett trough" refer to a device, usually made of teflon, that is used to produce Langmuir films. The device contains a reservoir that holds an aqueous solution and moveable barriers to compress film material that are layered onto the aqueous solution (See e.g., Roberts, *Langmuir-Blodgett Films,* Plenum, New York, [1990]).

As used herein, the term "domain size" refers to the typical length between domain boundaries.

As used the terms "conjugated backbone" and "polymer backbone" refer to the ene-yne polymer backbone of polymerized monomers that, on a macroscopic scale, appears in the form of physical ridges or striations. The term "polymer backbone axis" refers to an imaginary line that runs parallel to the conjugated backbone. The terms "intrabackbone" and "interbackbone" refer to the regions within a given polymer backbone and between polymer backbones, respectively. The backbones create a series of lines or "linear striations," that extend for distances along the template surface.

As used herein, the term "bond" refers to the linkage between atoms in molecules and between ions and molecules in crystals. The term "single bond" refers to a bond with two electrons occupying the bonding orbital. Single bonds between atoms in molecular notations are represented by a single line drawn between two atoms (e.g., $C_8$–$C_9$). The term "double bond" refers to a bond that shares two electron pairs. Double bonds are stronger than single bonds and are more reactive. The term "triple bond" refers to the sharing of three electron pairs. As used herein, the term "ene-yne" refers to alternating double and triple bonds. As used herein the terms "amine bond," "thiol bond," and "aldehyde bond" refer to any bond formed between an amine group (i.e., a chemical group derived from ammonia by replacement of one or more of its hydrogen atoms by hydrocarbon groups), a thiol group (i.e., sulfur analogs of alcohols), and an aldehyde group (i.e., the chemical group —CHO joined directly onto another carbon atom), respectively, and another atom or molecule.

As used herein, the term "covalent bond" refers to the linkage of two atoms by the sharing of two electrons, one contributed by each of the atoms.

As used the term "absorption" refers, in one sense, to the absorption of light. Light is absorbed if it is not reflected from or transmitted through a sample. Samples that appear colored have selectively absorbed all wavelengths of white light except for those corresponding to the visible colors that are seen.

As used herein, the term "spectrum" refers to the distribution of light energies arranged in order of wavelength.

As used the term "visible spectrum" refers to light radiation that contains wavelengths from approximately 360 nm to approximately 800 nm.

As used herein, the term "ultraviolet irradiation" refers to exposure to radiation with wavelengths less than that of visible light (i.e., less than approximately 360 nM) but greater than that of X-rays (i.e., greater than approximately 0.1 nM). Ultraviolet radiation possesses greater energy than visible light and is therefore, more effective at inducing photochemical reactions.

As used herein, the term "chromatic transition" refers to the changes of molecules or material that result in an alteration of visible light absorption. In some embodiments, chromatic transition refers to the change in light absorption of a sample, whereby there is a detectable color change associated with the transition. This detection can be accomplished through various means including, but not limited to, visual observation and spectrophotometry.

As used herein, the term "thermochromic transition" refers to a chromatic transition that is initiated by a change in temperature.

As used herein, the term "solid support" refers to a solid object or surface upon which a sample is layered or attached. Solid supports include, but are not limited to, glass, metals, gels, and filter paper, among others. "Hydrophobized solid support" refers to a solid support that has been chemically treated or generated so that it attracts hydrophobic entities and repels water.

As used herein, the phrase "solid sensor platforms" refers to any solid support used for immobilizing sensor material.

As used herein, the term "film-ambient interface" refers to a film surface exposed to the ambient environment or atmosphere (i.e., not the surface that is in contact with a solid support).

As used herein, the term "formation solvent" refers to any medium, although typically a volatile organic solvent, used to solubilize and distribute material to a desired location (e.g., to a surface for producing a film or to a drying receptacle to deposit liposome material for drying).

As used herein, the term "micelle" refers to a particle of colloidal size that has a hydrophilic exterior and hydrophobic interior.

As used herein, the term "topochemical reaction" refers to reactions that occur within a specific place (e.g., within a specific portion of a molecule or a reaction that only occurs when a certain molecular configuration is present).

As used herein, the term "molding structure" refers to a solid support used as a template to design material into desired shapes and sizes.

As used herein, the terms "array" and "patterned array" refer to an arrangement of elements (i.e., entities) into a material or device. For example, combining several types of biopolymeric material with different analyte recognition groups into an analyte-detecting device, would constitute an array.

As used herein the term "interferants" refers to entities present in an analyte sample that are not the analyte to be detected and that, preferably, a detection device will not identify, or would differentiate from the analyte(s) of interest.

As used herein, the term "badge" refers to any device that is portable and can be carried or worn by an individual working in an analyte detecting environment.

As used herein, the term "device" refers to any apparatus (e.g., multi-well plates and badges) that contain biopolymeric material. The biopolymeric material may be immobilized or entrapped in the device. More than one type of biopolymeric material can be incorporated into a single device.

As used herein, the term "halogenation" refers to the process of incorporating or the degree of incorporation of halogens (i.e., the elements fluorine, chlorine, bromine, iodine and astatine) into a molecule.

As used herein, the term "aromaticity" refers to the presence of aromatic groups (i.e., six carbon rings and derivatives thereof) in a molecule.

As used herein, the phrase "water-immiscible solvents" refers to solvents that do not dissolve in water in all proportions. The phrase "water-miscible solvents" refers to solvents that dissolve in water in all proportions.

As used herein, the terms "positive," "negative," and "zwitterionic charge" refer to molecules or molecular groups that contain a net positive, negative, or neutral charge, respectively. Zwitterionic entities contain both positively and negatively charged atoms or groups whose charges cancel (i.e., whose net charge is 0).

As used herein, the term "biological organisms" refers to any carbon-based life forms.

As used herein, the term "in situ" refers to processes, events, objects, or information that are present or take place within the context of their natural environment.

As used the term "aqueous" refers to a liquid mixture containing water, among other components.

As used herein, the term "solid-state" refers to reactions involving one or more rigid or solid-like compounds.

As used herein, the term "regularly packed" refers to the periodic arrangement of molecules within a compressed film.

As used herein, the term "filtration" refers to the process of separating various constituents within a test sample from one another. In one embodiment, filtration refers to the separation of solids from liquids or gasses by the use of a membrane or medium. In alternative embodiments, the term encompasses the separation of materials based on their relative size.

As used herein, the term "sample" is used in its broadest sense. In one sense it can refer to a biopolymeric material. In another sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water, crystals and industrial samples. These examples are not to be construed as limiting the sample types applicable to the present invention.

GENERAL DESCRIPTION OF THE INVENTION

In the past few decades, new types of organic polymers such as polyacetylene, polydiacetylene, polypyrrole, polyaniline, and polyphenylene have received increased attention due to the high demand for materials capable of performing various functions.

Important properties of these materials include electroconductivity, liquid crystalinity, nonlinear optical properties, and novel chromatic properties (See e.g., Skotheim, T. A., [ed.], "*Handbook of Conducting Polymers*," Marcel Dekker, New York [1986]; Bredas, J. L., and Silbey, R. [eds.], "*Conjugated Polymers*," Kluwer Acad. Publ., Dordrecht. [1990]; Frechette et al., "Monomer reactivity vs. Regioregularity in polythiophene derivatives," *Macromol. Chem. Phys.*, 198:1709–1722 [1990]; and Roncali, J., "Conjugated poly(yhiopheno): synthesis, functionalization, and applications," *Chem. Rev.*, 92:711–738 [1992]). These conjugated polymers exhibit high electrical conductivity with good thermal stability. For their preparation, synthetic efforts were geared towards minimizing structural defects (e.g., broad molecular weight distribution, branching, crosslinking, etc.) (See e.g., Roncali, J., *Chem. Rev.*, 92:711–738 [1992]). Among them, polythiophene is one of the most important classes of π-conjugated polymers. Due to planar-nonplanar conformational transitions of the π conjugated system, these materials exhibit a variety of optical transitions upon external stimuli such as heat (See e.g., Leclerc et al., "Chromic phenomena in neutral polythiophene derivatives," *Macromol. Chem. Phys.*, 197:2077–2087 [1996]; Roux et al., "Polythiophene derivatives: smart materials," *Polymer News*, 19:6–10 [1994]; Levesque, I., and Leclerc, M., "Ionochromic effects in regioregular ether-substituted polythiophenes," *J. Chem. Soc. Chem. Commun.*, 7:2293–2294 [1995]; and Graf et al., "From monomers to π-stacks: A comprehensive study of the structure and properties of monomeric, π-dimerized, and π-stacked forms of the cation radical of 3',4'-dibutyl-2',5'-diphenyl-2,2':5',2'-terthiophene," *J. Am. Chem. Soc.*, 119:5888–5899 [1997]), light (See e.g., Patil et al., "Optical properties of conducting polymers," *Chem. Rev.*, 88:183–200 [1988]), metals (See e.g., Masella, M. J., and Swager, T. M., "Designing conducting polymer-based sensors: selective ionochromic response in crown ether containing polythiophenes," *J. Am. Chem. Soc.*, 115:12214–12215 [1993]; and Crawford et al., "$Na^+$ specific emission changes in an ionophoric conjugated polymer," *J. Am. Chem. Soc.*, 120:5187–5192 [1998]), chemicals (See e.g., McCullough et al., "Self-assembly and disassembly of regioregular, water soluble polythiophenes: chemoselective ionchromatic sensing in water," *J. Am. Chem. Soc.*, 119:633–634 [1997]), and proteins (See e.g., Faid, K., and Leclerc, M., "Functionalized regioregular polythiophenes: towards the development of biochromic sensors," *J. Chem. Soc., Chem. Commun.*, 2761–2762 [1996]; Pande et al., "A biotinylated undecylthiophene copolymer bioconjugate for surface immobilization: creating an alkaline phosphatase chemiluminescence-based biosensor," *Bioconjugate Chem.*, 7:159–164 [1996]; and Charych et al., "Direct colorimetric detection of a receptor-ligand interaction by a polymerized bilayer assembly," *Science*, 261:585–588 [1993]). These effects have been termed thermochromism, photochromism, ionochromism, or biochromism, respectively. These chromic transitions are strongly correlated with the electronic structure and the conformation of the polymer backbone. Indeed, theoretical studies have shown that a high degree of planarity along the polymer chains leads to better electrical properties (See e.g., Bredas, J. L., "Relationship between band gap and bond length alternation in organic conjugated polymers, *J. Chem. Phys.*, 82:3809–3811 [1985]). However, the rearrangement of the polymer backbone also strongly depends on the conformational state of the side chains (See e.g., Patil et al., *Chem. Rev.*, 88:183–200 [1988]). In addition, aggregation of polythiophene chains induces the formation of π-stacks in the macromolecular assembly and generates enhanced electronic and photonic properties (See e.g., Graf et al., *J. Am. Chem. Soc.*, 119:5888–5899 [1997]; McCullough, R. D., "The chemistry of conducting polythiophenes," *Adv. Mater.*, 10:93–116 [1998]; and Hernandez, V., "Confinement potential and π-electron delocalization in polyconjugated organic materials," *Phys. Rev. B* 50, 9815–9823 [1994]). Therefore, the degree of π-conjugation of the polymer chains and their susceptibility to external stimuli are important if the material is to be used as a sensory device (See e.g., Marsella et al., "Design of chemoresistive sensory materials: polythiophene-based pseudopolyrotaxanes," *J. Am. Chem. Soc.*, 117:9832–9841 [1995]).

The present invention relates to methods and compositions for the direct detection of analytes using observable spectral changes in biopolymeric systems. In particular, the present invention allows for the direct colorimetric detection of analytes using color changes that occur in polymer systems (e.g., glycopolythiophenes) in response to selective binding of analytes.

The present invention provides methods and compositions related to polymerized biological material that incorporate ligands (e.g., proteins, carbohydartes, lipids, etc.) with affinity for analytes. Upon associating with the analytes (e.g., binding of the analyte to a ligand), the biopolymeric material undergoes a detectable (e.g., visually detectable) color change. The present invention provides for the direct detection of the presence of a wide range of analytes due to such changes in color, including, but not limited to, small molecules, pathogenic and non-pathogenic organisms, toxins, membrane receptors, membrane fragments, volatile organic compounds (VOCs), enzymes, enzyme substrates, drugs, antimicrobials, antibodies, antigens, viruses, and other materials of interest. Results can be interpreted by an untrained observer, and the methods can be conducted under ambient conditions, making them amenable to numerous uses including, but not limited to, home testing diagnostics, detection of air-borne or water-borne pathogens for military applications, detection of indicator organisms (i.e., organisms that indicate the presence of contamination), doctor's office or point of care testing, and many other applications. The present invention provides analyte detecting technology that does not require an energy source and is cost-efficient, stable, accurate, reliable, consistent, and robust. These enhanced qualities provide an ideal basis for use in screening new compound libraries (e.g., drug screens), drug testing, fiber optic methods for remote sensing, water supply testing, and any application in which a rapid and accurate colorimetric screen is desired.

The present materials exhibit rapid response times, selectivity, and optical signals that are easily monitored. As free-floating aggregates in solution, these lipid-based detectors show promise as simple assay systems. As immobilized films, liposomes, or other forms, these detectors provide durable, robust colorimetric sensors that can be easily incorporated into small detection devices (e.g., a detection badge, portable detection kits, and the like). The present invention provides embodiments in which these biopolymeric materials incorporate ligands, such as peptides, proteins, antibodies, carbohydrates, and lipids. These ligands allow for the direct colorimetric detection of a broad range of analytes (e.g. ions, carbohydrates, proteins, lipids, and antigens), while also providing specificity by detecting the interaction between individual ligand types and only one or a small class of analytes. The present invention further contemplates biopolymeric materials containing multiple ligands for the detection of larger classes of analytes.

The present invention also contemplates an array of biopolymeric materials incorporated into a single device, such that each individual section of biopolymeric material responds to a different analyte. Such arrays can be designed so that the presence of a given analyte will produce a color change in a known location in the device, or that will produce a color change specific to the given analyte (e.g., purple to orange for analyte X and blue to red for analyte Y). It is also contemplated that other arrays will be used with the present invention, including such easily understood patterns as a "+" sign to indicate that presence of a particular substance or compound. It is not intended that the present invention be limited to any particular array design or configuration.

Thus, the present invention provides methods and compositions that fulfill many of the goals of the analyte detection field and overcomes many of the disadvantages of currently available technologies. Moreover, the present invention provides significant advantages over previously used biosensors, as the embodiments of the present invention are not dependent upon transducing technologies. Many proposed biosensors cannot be used because of difficulties in transducing the molecule recognition event into a measurable signal. Additionally, the transducers of previously developed devices add cost, create a requirement for a power source, are more difficult to use by untrained personnel, and are limited in terms of miniaturization and portability. Also, many biosensors do not display the long term stability and robustness of the present invention.

DETAILED DESCRIPTION OF THE INVENTION

The present invention comprises methods and compositions related to biopolymeric materials that change color in the presence of analyte. These biopolymeric materials comprise many forms including, but not limited to, polymers, films, vesicles, tubules, and multilayered structures. These materials are comprised of polymerized monomers. In some embodiments, the biopolymeric materials comprise more than one species of polymerizable monomer in a composition with one or more monomers that lack polymerizable groups. In other embodiments, the materials further comprise dopant material(s) that alter the properties of the sensor. Dopants include, but are not limited to, polymerizable self-assembling monomers, non-polymerizable self-assembling monomers, polymerizable non-self-assembling monomers, non-polymerizable non-self-assembling monomers, lipids, cholesterols, membrane components and any other molecule that optimize the biopolymeric material (e.g., material stability, durability, colorimetric response, and immobilizability). The biopolymeric material may further comprise ligands (e.g., proteins, carbohydrates, lipids, etc.). The ligands provide recognition sites for analytes, such that binding of the analyte to the ligand results in a color change of the biopolymeric material. The use of particular ligands can be used to selectively detect the presence of a specific analyte(s). The various embodiments of the present invention provide the ability to colorimetrically detect a broad range of analytes. The analytes either interact directly with the monomers or with ligands that are linked to or associated with the monomers. With certain biopolymeric materials, a color transition occurs upon analyte binding that can be viewed by simple visual observation or, if desired, by color sensing equipment. The present invention provides a variety of means of immobilizing the biopolymeric material to provide stability, durability, and ease of handling and use. In some embodiments, a variety of different polymeric materials are combined into a single device to produce an array. The array can be designed to detect and differentiate differing types or quantities of analytes (i.e., the array can provide quantitative and/or qualitative data).

In preferred embodiments of the present invention, a novel family of glycopolythiophenes containing carbohydrates (e.g., sialic acid or mannose ligands) were prepared by two strategies: graft-conjugation of carbohydrate ligands, and oxidative copolymerization with methyl thiopheneacetate. In the latter case, the spacer-length between the polymer backbone and the ligand was varied to optimize binding interactions. In certain of these embodiments, the glycopolymers were blue-shifted (absorbance of ca. 400 nm) relative to the corresponding homo-polythiophenes (absorbance ca. 440 nm), suggesting a twisted conformation for the glycopolymers. While an understanding of the mechanism of the present invention is not required, and the present invention is not intended to be limited to any particular mechanism, the altered conformation is likely due to electrostatic and steric interactions among the polymer chains and/or hydroxyl groups in the carbohydrate ligand. Conformational changes in the polythiophene backbone were detected by the binding of specific receptors; lectins (wheat germ agglutinin, concanavalin A), Influenza virus and *E. coli*. The decreased steric interactions derived from the ligands generates a red-shift in the visible absorption of the polymer backbone. From these results, it is shown that these conjugated polymeric systems offer a potentially new platform for diagnostic applications amenable to situations where simple, rapid, accurate, and cost-efficient detection is required.

Certain applications of polythiophene-based biosensors of the present invention require that the materials be tailored to specific biological environments. This typically requires the incorporation of biologically active species, such as proteins, peptides lipids, or carbohydrates in the polymeric system. In particular, carbohydrates are attractive because they are relatively small when compared to proteins and are expressed externally from the cell surface, for example, as a component of glycoproteins, glycolipids, and capsular polysaccharide (See e.g., Sharon, N., "*Complex Carbohydrates: Their Chemistry, Biosynthesis and Functions*," Addison-Wesley, Reading, Mass. [1975]). These carbohydrates are involved in key recognition events (See e.g., Reutter et al., In "*Sialic acids, Chemistry, Metabolism, and Function*," Cell biology monograph series, Vol. 10, R. Schauer, [ed.], Springer-Verlag, Vienna [1982]; Goldstein, I. J., and Poretz, R. D., In "*The lectins. Properties, Functions and Applications in Biology and Medicine*," Liener, I. E.; Sharon, N.; Goldstein, I. J. [eds.], Academic press, Orlando, Fla. [1986]; and Sharon, N., and Lis, H., "Carbohydrates in cell recognition," *Scientific American*, 82–89 [January 1993]) with a variety of receptor proteins such as hormones, enzymes, toxins, lectins, antibodies, viruses and bacteria. Carbohydrates are also involved in numerous biological processes (See e.g., Lee, Y. C., and Lee, Reiko T., "*Neoglycoconjugates: preparation and applications*," Academic press [1994]) such as cell growth, recognition and differentiation, cancer metastasis, inflammation and pathogen-entry.

Thus, carbohydrate moieties are excellent tools for creating new types of biochromic polythiophene materials. For example, an analog of sialic acid is the receptor-specific carbohydrate for the Influenza virus hemagglutinin (See e.g., Reutter et al., Cell biology monograph series, Vol. 10, R. Schauer, [ed.], Springer-Verlag, Vienna [1982]; Goldstein, I. J., and Poretz, R. D., In "*The lectins. Properties, Functions and Applications in Biology and Medicine*," Liener, I. E.; Sharon, N.; Goldstein, I. J. [eds.], Academic press, Orlando, Fla. [1986]; Sharon, N., and Lis, H., *Scientific American*, 82–89 [January 1993]; Toogood et al., "Monovalent sialosides that bind tightly to influenza A virus," *J. Med. Chem.*, 34:3138–3140 [1991]; Roy et al., "Synthetic oligosaccharides: indispensable probes for the life sciences," *ACS Symposium Series*, 560:104–119 [1993]; and Klenk, H. D., and Rott, R., "The molecular biology of influenza virus pathogenicity," *Advances in Virus Research*, 34:247–281 [1988]). In addition, certain mannose residues recognize some bacterial species, such as *E. coli* and Salmonella (See e.g., Orndorff, P. E., and Falkow, S., "Identification and characterization of a gene product that regulates type I piliation in *Escherichia coli*," *J. Bacterology*, 160:61–66 [1984]; Betozzi, C. R., and Bednarski, M. D., "A receptor-mediated immune response using synthetic glycoconjugates," *J. Am. Chem. Soc.*, 114:5543–5546 [1992]; Old, D. C., "Inhibition of the interaction between fimbrial haemagglutinins and erythrocytes by D-mannose and other carbohydrates," *J. Gen. Microb.*, 71:149–157 [1972]; Firon et al., "Carbohydrate-binding sites of the mannose-specific fimbrial lectins of enterobacteria," *Infection and Immunology*, 43:1088–1090 [1984]; Venegas et al., "Binding of type 1-piliated *Escherichia coli* to Vaginal mucus," *Infection and Immunology*, 63:416–422 [1995]; and Madison et al., "Type I fimbrial shafts of *Escherichia coli* and klebsiella pneumoniae influence sugar-binding specificities of their fimH adhesins," *Infection and Immunology*, 62:843–848 [1994]). In particular, Type I piliated *E. coli* is a pathogen responsible for many urinary tract infections, and is a mannose-specific bacteria (See e.g.,Old, D. C., "*J. Gen. Microb.*, 71:149–157 [1972]; Firon et al., *Infection and Immunology*, 43:1088–1090 [1984]; and Madison et al., *Infection and Immunology*, 62:843–848 [1994]).

Considering the interactions of sialic acid and mannose toward these specific pathogen proteins, a series of new thiophene-carbohydrate monomers were designed and synthesized with well-defined spacer lengths (side chains) to optimize protein binding. In preferred embodiments, subsequent co-polymerization of the thiophene-carbohydrate monomer with thiophene-acetic acid as a co-monomer gave a series of novel glycopolythiophenes (glyco-PTs) (FIG. 1). In addition, the multivalent display of carbohydrates on the glyco-PTs overcomes the characteristic low binding affinity of the individual carbohydrates to their receptor proteins. The glyco-PTs were tested for their ability to undergo absorption shifts after the addition of proteins. The mannose glyco-PTs were studied with Concanavalin A (Con A), biotin labeled Con A and *E. coli* (HB101 strain), whereas the sialic acid-glyco-PTs were investigated with *Triticum Vulgaris* (Wheat germ) and Influenza virus (A/B).

The ability of the present materials in preferred embodiments to detect lectins, influenza virus and *E. coli* was evaluated by visible absorption spectrometry. While an understanding of the mechanism of the present invention is not needed, and the present invention is not intended to be limited to any particular mechanism, it is believed that intermolecular interactions play a role in red shifts observed upon interaction with the cognate receptors. For example, upon ligand-receptor binding intermolecular interactions that produce a twisted polymer backbone are disrupted, and a more planar polymer backbone results. In general, the longer the side chain between the receptor and the polymer backbone, the greater the absorption maximum shift. This may be related to optimized fit of the ligand to the receptor pocket. These effects have been amplified by the preparation of more regioregular species, and thiophenes oligomers. The present invention describes optimization of these systems to achieve enhanced detection of biological macromolecules.

In some embodiments of the present invention, the biopolymeric materials comprise free polymers, that can adapt to different conformations. For example, in a preferred embodiment, in the unbound state the glycopolythiophene assemblies may curl up on themselves (e.g., the sugars can H-bond with each other) twisting the backbone and making it less conjugated (i.e., blue shift in absorption). While an understanding of the mechanism of the present invention is not needed, and the present invention is not intended to be limited to any particular mechanism, it is believed that when something binds to this polymer, it breaks up the inter-polymer interactions, effectively stretching it out and extending the conjugated length, thereby absorbing more red light (i.e., red shift in absorption) and appearing blue in color.

In preferred embodiments of the present invention, water-soluble glycopolythiophenes containing sialic acid or mannose ligands were synthesized by oxidative co-polymerization of thiopheneacetic acid (compound 6) and thiophene-carbohydrate monomers. The ability of these materials to detect lectins, influenza virus and *E. coli* was evaluated by visible absorption spectrometry. The biochromic properties were dependent on the structure of polymers and the nature of the binding receptors (e.g., divalent versus multi-valent). While an understanding of the mechanism of the present invention is not needed, and the present invention is not intended to be limited to any particular mechanism, it is believed that due to the presence of the carbohydrate ligands on the polymer backbone, each chain has lower degree of $\pi$-conjugation than the corresponding homopolythiophene. These intermolecular interactions play an important role in the red shifts observed upon interaction with the cognate receptors. Once the receptor protein binds, the intermolecular interactions that produce a twisted polymer backbone are disrupted, and a more planar polymer backbone results. In general, the longer the side chain between the carbohydrate and the polymer backbone, the greater the absorption maximum shift. This may be related to optimized fit of the ligand to the receptor pocket. These effects have been amplified by the preparation of more regioregular species.

The description of the invention is divided into: I. Carbohydrate Monomers; II. Polymerization; III. Biochromic Effects; IV. Dopants; V. Ligands; VI. Detection Of Analytes; VII. Immobilization of Biopolymeric Materials; and VIII. Arrays.

I. Carbohydrate Monomers

Figure 2:
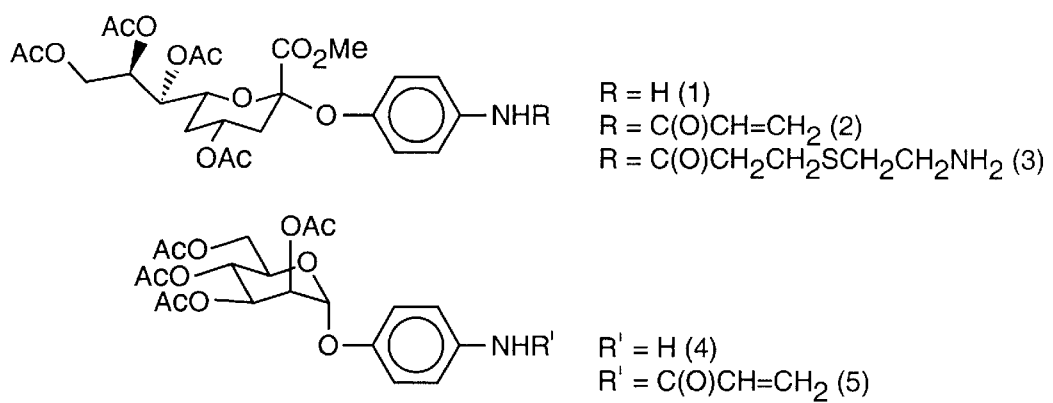
FIG. 2 shows the structure of various carbohydrate ligands bearing aromatic aglycons (compounds 1, 2, 3, 4, and 5).
Figure 3:
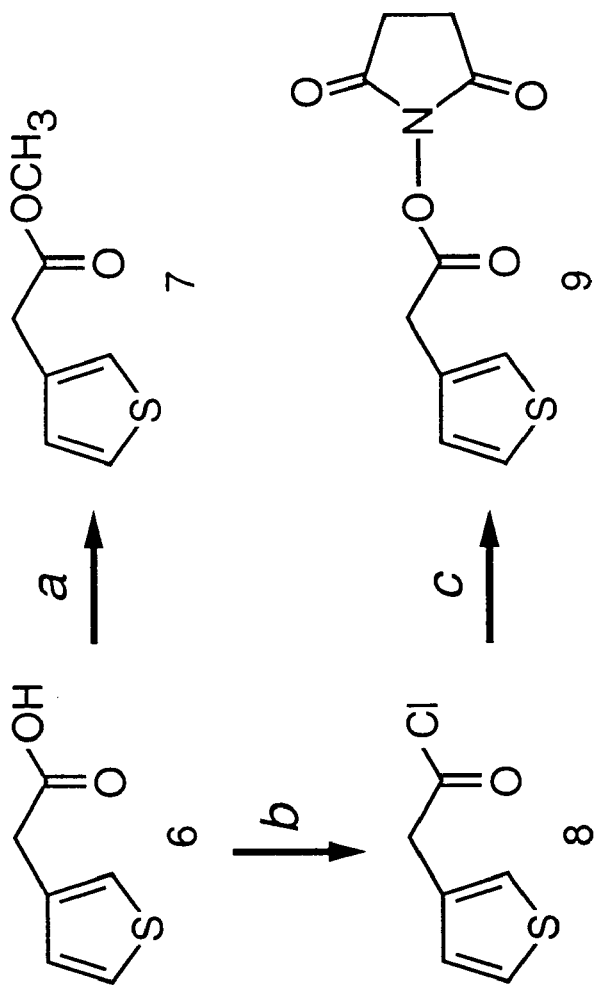
FIG. 3 shows a chemical synthesis for thiophene esters (compounds 6, 7, 8, and 9).

In preferred embodiments, functionalized sialic acid and mannose moieties at O-linked aromatic aglycon (compounds 1, 2, 3, 4 and 5) were prepared according to literature procedures (See, Roy et al., "Synthesis of esterase-resistant 9-O-acetylated polysialoside as inhibitor of influenza C virus hemagglutinin," *Angew. Chem. Int. Ed. Engl.*, 31:1478–1481 [1992]; and Page et al., "Synthesis and lectin binding properties of dendritic mannopyranoside," *Chem. Commun.*, 1913–1914 [1996]) (FIG. 2). FIG. 2 shows the structure of various carbohydrate ligands bearing aromatic aglycons (compounds 1, 2, 3, 4, and 5). In preferred embodiments, aromatic aglycon was used as the mannose ligand since a hydrophobic pocket mainly composed of tyrosine (Tyr) residues in the mannose specific protein stabilizes the carbohydrate by $\pi$-$\pi$ interactions with the hydrophobic substituent of the aglycon (See, Hardman, K. D., "the carbohydrate binding site of concanavalin A," *ACS Symp. Ser.*, 88:12–26 [1979]). For sialic acid, the aromatic aglycon prevents the neuraminidase of the influenza virus, from cleaving the O-linked glycosidic bond (See, Roy et al., *Angew. Chem. Int. Ed. Engl.*, 31:1478–1481 [1992]; Toogood et al., *J. Med. Chem.*, 34:3138–3140 [1991]; Klenk, H. D., and Rott, R., *Advances in Virus Research*, 34:247–281 [1988]); and Spaltenstein, A., and Whitesides, G., "Polyacrylamides bearing pendant $\alpha$-sialoside groups strongly inhibit agglutination of erythrocytes by influenza virus," *J. Am. Chem. Soc.*, 113:686–687 [1991]). On the basis of the fixed carbohydrate structures, two series of thiophene-carbohydrate monomers were synthesized, derived from the thiophene esters shown in FIG. 3. FIG. 3 shows a chemical synthesis for thiophene esters (compounds 6, 7, 8, and 9).

(The reaction conditions specified in FIG. 3(a) are as follows: SOCl$_2$/MeOH, 0° C. to room temperature over 3 h, 88% yield; FIG. 3(b) are as follows: SOCl$_2$/dioxane at room temperature; FIG. 3(c) are as follows: NHS, DIPEA/CHCl$_3$, 0° C.; 75% yield).

Figure 4:
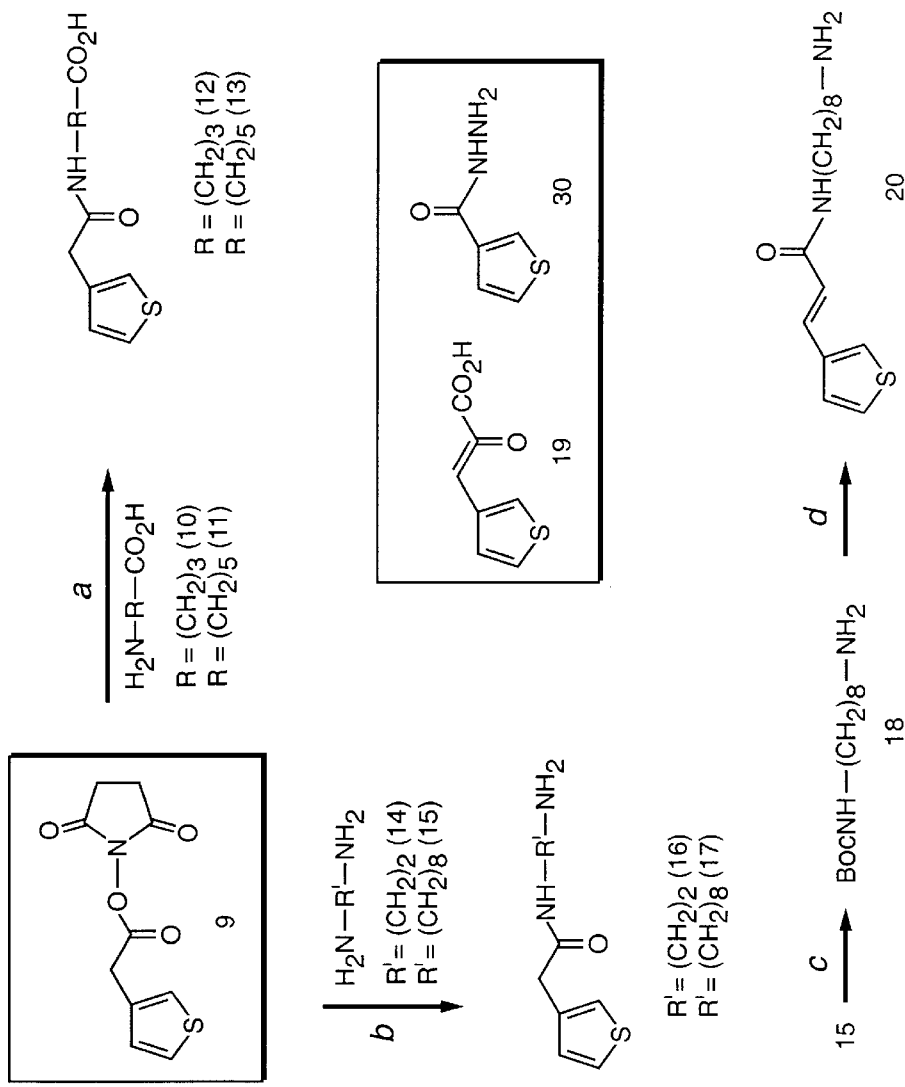
FIG. 4 shows a chemical synthesis of acid-base functionalized thiophenes (compounds 10–20, and 30).

In the first set of experiments, amine and carboxylic acid terminated thiophene intermediates were prepared (FIG. 4) and subsequently coupled with carbohydrate moieties. In the second set, the distance between thiophene and carbohydrate was extended by iminothiolane hydrochloride (compound 30) and a thiol was generated after extension. (The reaction conditions specified in FIG. 4(a) are as follows: cat. DIPEA/CHCl$_3$, r.t., 95% yield; FIG. 4(b) are as follows: CHCl$_3$ (highly diluted), r.t., overnight, 83–96% yield; FIG. 4(c) are as follows: BOC-ON, Et$_3$N/CHCl$_3$, r.t., 52% yield; FIG. 4(d)(i) are as follows: 3-(3-Thienyl)acrylic acid (compound 19), HOBt/EDC, DIPEA, CHCl$_3$, r.t., 6 h, 93% yield; FIG. 4(d)(ii) are as follows: 30% TFA/CH$_2$Cl$_2$, r.t., 3 h, 93% yield; FIG. 4(d)(iii) are as follows: 1 M NaOH, quantitative). These thiols were prepared in situ and coupled with compounds 2 or 5 by Michael type addition to give another set of thiophene-carbohydrate monomers. The two types of carbohydrate moieties are summarized in FIG. 5 and FIG. 6. Commercially available 3-thiopheneacetic acid (compound 6) (Acros Organics, Fisher Scientific, Pittsburgh, Pa.) was converted into the corresponding methyl ester (compound 7) in 88% yield by thionyl chloride in methanol. Thiopheneacetyl chloride (compound 8) was prepared in situ, by thionyl chloride in dioxane. Direct addition of N-hydroxysuccinimide (NHS) in the presence of diisopropylethylamine (DIPEA) at 0° C. afforded thiophene active ester (compound 9) in 75% overall yield. Compound 9 was stable under dry conditions and could be prepared in bulk quantities.

Figure 5:
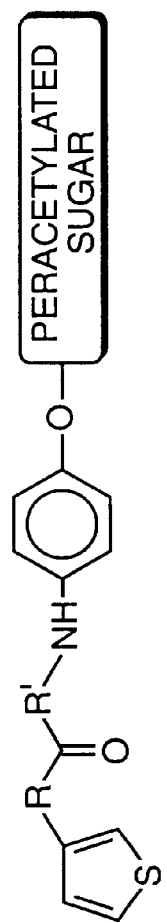
FIG. 5 shows various thiophene-carbohydrate monomers prepared by the peptide coupling method (compounds 21–29).

Carboxylic acid functionalized thiophenes, compounds 12 and 13, with hydrocarbon spacers, were prepared by nucleophilic addition of bifunctionalized compounds 10 and 11 to compound 9 in 95% yields (FIG. 4). In a similar manner, compound 9 was reacted with diamine compounds 14 and 15 under highly dilute conditions. Dimerized byproduct was removed by simple silica gel chromatography to give the amine compounds 16 and 17 in 83 and 96% yields, respectively. Compound 17 was obtained from compound 6 and mono-Boc protected compound 18 by peptide coupling and subsequent deprotection by 30% trifluoroacetic acid (TFA) in CH$_2$Cl$_2$. To extend the π-conjugation in the polymer to the spacer 3-(3-thienyl)acrylic acid (compound 19) was used, followed by treatment with TFA to afford the thiophene free amine (compound 20), in 93% yield. No polymerization of the acrylic functional group was detected during synthesis and the results were confirmed by NMR. Carboxylic acid functionalized thiophene compounds 6, 12, 13 and 19, were coupled with carbohydrate moieties, compounds 1, 3 or 4 by the O-benzotriazol-1-yl-N,N,N',N'-tetramethyluronium tetrafluoroborate (TBTU) strategy to afford the series of thiophene-spacer (side chain)-carbohydrates, compounds 21, 22, 23, 24, 25 for sialic acid and compounds 26, 27, 28 and 29 for mannose. The yields were 60–90% for the sialic acid residue and 70% quantitative for the mannose residue, respectively (FIG. 5).

Figure 6:
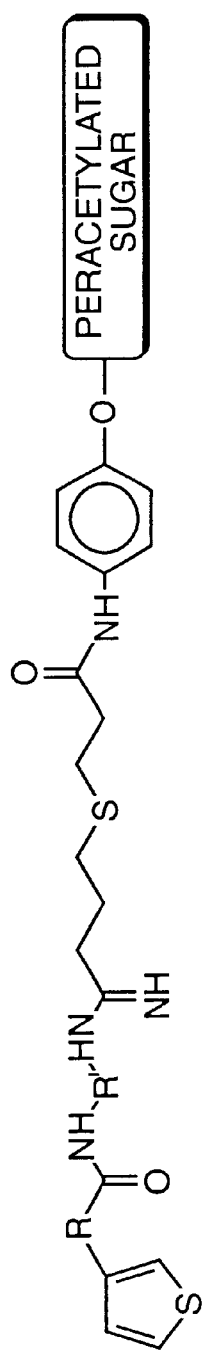
FIG. 6 shows various thiophene-carbohydrate monomers prepared using the imminothiolane hydrochloride method (compounds 32–38).

For a mimic of the lipid-carbohydrate monomer used in previous studies of biochromism (See e.g., Charych et al., Science, 261:585–588 [1993]; and Lio et al., "Molecular imaging of thermochromic carbohydrate-modified polydiacetylene thin films," Langmuir, 13:6524 [1997]), more elongated spacers were designed and synthesized using the iminothiolane hydrochloride (compound 31) strategy (FIG. 6). Ring opening nucleophilic addition of compound 31 was initiated by the free amine bearing thiopene derivatives (compounds 16, 17, 20 and 30) in the presence of diisopropylethylamine (DIPEA) and degassed methanol to generate a series of mercapto-thiophene intermediates. Subsequent addition of compounds 2 or 5 derived Michael type addition of a thiol to the acrylamido functional group to afford the second set of thiophene-spacer-carbohydrate species, compounds 32, 33, 34 for sialic acid, and compounds 35, 36, 37, 38 for mannose in 51–78% and 35–53% yields, respective. All structures were confirmed by NMR ($^1$H, $^{13}$C) and mass spectra.

II. Polymerization

Figure 7:
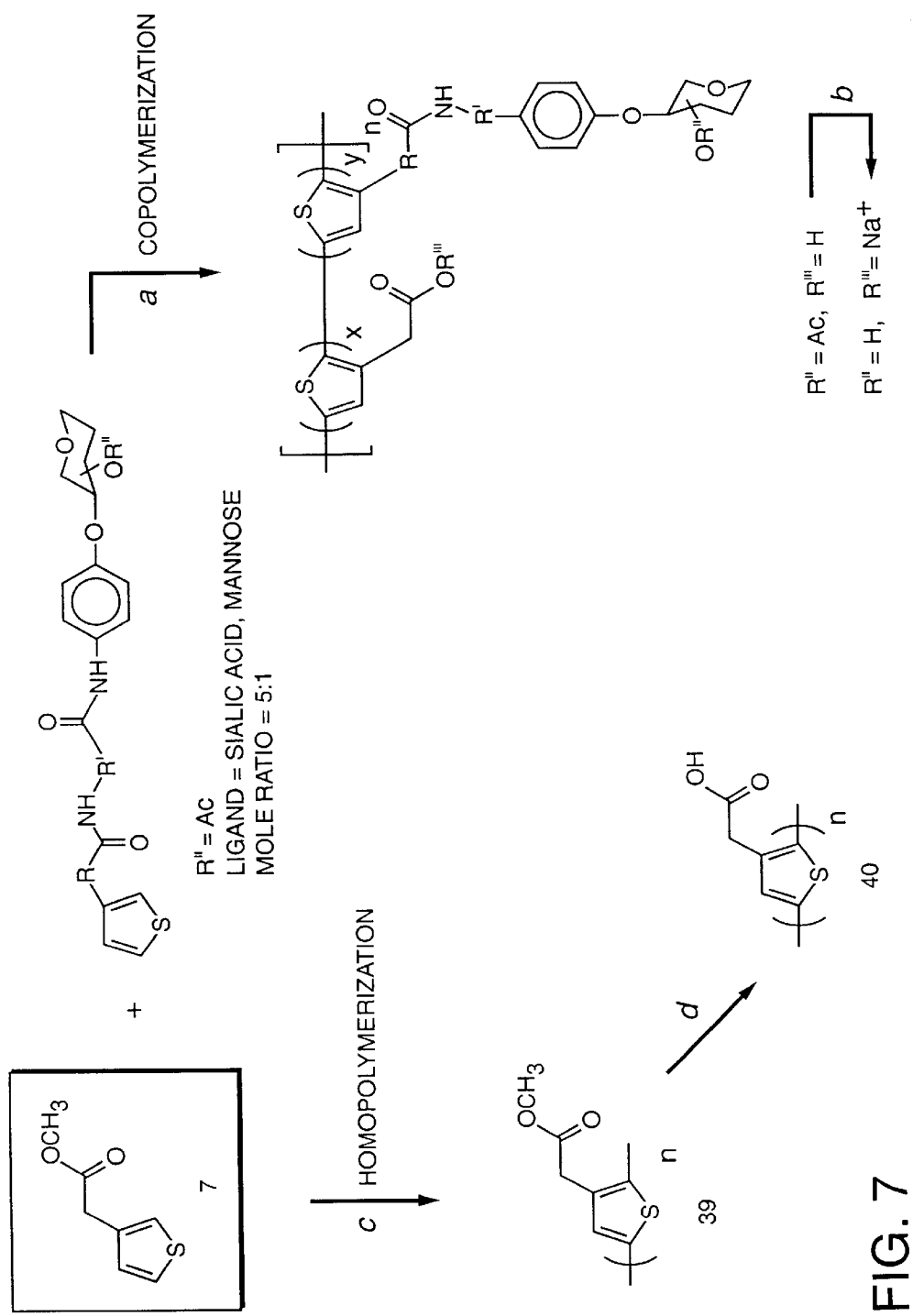
FIG. 7 shows a chemical synthesis using the oxidative polymerization with $FeCl_3$ method (compounds 39 and 40).

The formation of carbohydrate-modified polythiophene was carried out primarily by the (co-) polymerization of the thiophene-carbohydrate monomers, and the thiophene methyl ester (compound 7), using FeCl$_3$ as a promoter (FIG. 7). (The reaction conditions specified in FIG. 7(a)(i) are as follows: FeCl$_3$, dry CHCl$_3$, N$_2$, r.t., 2–3 days; FIG. 7(a)(ii) are as follows: Soxhlet extraction/MeOH; FIG. 7(b) are as follows: MeO$^-$Na$^+$/MeOH/CHCl$_3$ (ph 9), 7 h; FIG. 7(b)(ii) are as follows: 0.3 M NaOH (aq), r.t., 5–10 h; FIG. 7(b)(iii) are as follows: dialysis/water (MW 12,000 cutoff); FIG. 7(c)(i) are as follows: FeCl$_3$ (4 equiv), dry CHCl$_3$, N$_2$, r.t., 3 days; FIG. 7(c)(ii) are as follows: Soxhlet extraction/MeOH, 67% (w/w); FIG. 7(d)(i) are as follows: NaOH (1.2 equiv)/MeOH, reflux, 5 h; FIG. 7(d)(ii) are as follows: HCl, 0° C., 90% (w/w)).

The homopolymers, poly (methyl 3-thiopheneacetate) (compound 39) (FIG. 7), was prepared from chemical oxidative polymerization of compound 7 in CHCl$_3$ (See e.g. Leclerc et al., Macromol. Chem. Phys., 197:2077–2087 [1996]; Roux et al., Polymer News, 19:6–10 [1994]; Levesque, I., and Leclerc, M., J. Chem. Soc. Chem. Commun., 7:2293–2294 [1995]; Faid, K., and Leclerc, M.,J. Chem. Soc., Chem. Commun., 2761–2762 [1996]; and McCullough, R. D., and Loewe, R. D., "Enhanced electrical conductivity in regioselectively synthesized poly(3-alkylthiophenes)," J. Chem. Soc., Chem. Commun., 70–72 [1992]). Compound 39 was purified by Soxhlet extraction with methanol for 3 days to eliminate the low molecular weight portion and any residual promoter to afford 67% (w/w) yield. Subsequently, compound 39 was further refluxed in the presence of NaOH in methanol for 5 h and acidified with concentrated HCl at 0° C. to give compound 40 in 90% (w/w) yield.

A series of thiophene-carbohydrate monomers were co-polymerized with compound 7 by FeCl$_3$ in dry CHCl$_3$ followed by Soxhlet extraction with methanol to afford the corresponding glycopolythiophene derivatives in 50–76% (w/w) yields. The ratio of compound 7 to thiophene-carbohydrate applied was 5/1. The structural regularity of some glycopolythiophenes having reasonable solubility in organic solvent were determined by $^1$H-NMR spectral data. Mostly, they possessed a randomly distributed chain structure and presented a broad distribution of signals over the whole range of the spectra (See e.g., McCullough, R. D., and Loewe, R. D., J. Chem. Soc., Chem. Commun., 70–72 [1992]; Chen, T. A., and Rieke, R. D., "The first regioregular head-to-tail poly(3-hexylthiophene-2,5-diyl) and a regiorandom isopolymer: Ni vs. Pd catalyst of 2(5)-bromozincio-3-hexylthiophene polymerization," J. Am. Chem. Soc. 114, 10087–10088 [1992]; and McCullough et al., "Self-orienting head-to-tail poly(3-alkylthiophenes): new insights on structure-property relationships in conducting polymers," J. Am. Chem. Soc., 115:4910–4911 [1993]).

Conversion of these glycopolythiophenes into the corresponding de-protected analogues was accomplished as follows. Fully protected glycopolythiophenes were treated with MeO⁻ Na⁺ vin MeOH/CHCl₃ mixture for 7–9 h, and subsequently, an excess of aqueous NaOH was reacted for 5–10 h at room temperature depending on the polymers. The heterogeneous solution turned into a homogeneous red-brown solution when deesterification was complete. The solution was dialyzed (molecular weight 12,000 cut-off) against water to eliminate excess NaOH and low molecular weight portion and lyophilized to afford brownish solid, compounds 42, 43, 44, 45, 46, 47, 48 and, 49 for sialic acid-PTs in 31–50% (w/w) yields, and compounds 50, 51, 42, 53, 54, 55, 56 and 57 for mannose-PTs in 28–48% (w/w) yields, were obtained respectively (FIG. 8). However, these dried polymers were poorly soluble in aqueous solution again and NaOH was required to induce solubility.

In one case, the glycopolymer was prepared by graft conjugation of carbohydrate ligands to pre-formed polythiophene acetic acid (compound 40). Graft conjugation of carbohydrate moiety (compound 3) to polymer compound 40 was accomplished by TBTU strategy to afford 49% (w/w) yield. The ratio of carbohydrate/carboxylic acid units used in compound 40 was 1/3.

III. Biochromic Effects

As recently reported (See e.g., Faid, K., and Leclerc, M., *J. Chem. Soc., Chem. Commun.,* 2761–2762 [1996]), polythiophene derivatives that display biotin were synthesized and shown to undergo colorimetric transitions in response to binding of streptavidin. The degree of conjugation in the polythiophene backbone is influenced by external stimuli (See e.g., Leclerc et al., "Processing-induced chromism in thin films of polythiophene derivatives," *Macromol. Rapid Commun.,* 18:733–737 [1997]; Faid et al., "Chromic phenomena in regioregular and nonregioregular polythiophene derivatives," *Chem. Afater.,* 7:1390–1396 [1994]; Lee et al., "The effects of ester substitution and alkyl chain length on the properties of polythiophenes," *Synth. Met.,* 69:295–296 [1995]; Li et al., "A highly π-stacked organic semiconductor for thin film transistors based on fused thiophenes," *J. Am. Chem. Soc.,* 120:2206–2207 [1998]; and Roux, C., and Leclerc, M., "Rod-totail transition in alkoxy-substituted polythiophenes," *Macromolecules,* 25:2141–2144 [1992]) and usually involves planar-nonplanar transitions. Another important driving force for the conformational change of the polymer backbone is electrostatic interactions, leading to aggregation, gelation or even crystallization (See e.g., Pincus, P., and De Gennes, P. G., "Nematic polymers," *J. Polym. Sci., Polym. Symp.,* 65:85–90 [1978]). As reported by McCullough et al., (*J. Am. Chem. Soc.,* 119:633–634 [1997]), regio-regular polythiophenes having carboxylic acid side chains on an ethylene spacer, showed significant H-bonding that contributes to extended π-orbital overlap along the main chain. In that particular work, the absorption maximum of the polymer is 560 nm.

In preferred embodiments of the present invention, a non-regioregular polythiophene homopolymer derivative (compound 40), containing a methylene spacer between the backbone and the acid group showed a maximum absorption at 440 nm. This comparison suggests that regio-regularity and the nature of the functionalized side chain are important factors in determining the conformation of the polymer backbone (See e.g., Leclerc et al., "Processing-induced chromism in thin films of polythiophene derivatives," *Macromol. Rapid Commun.,* 18:733–737 [1997]; Faid et al., "Chromic phenomena in regioregular and nonregioregular polythiophene derivatives," *Chem. Afater.,* 7:1390–1396 [1994]; and Rughooputh et al., "Chromism of soluble polythiophenes," *J. Polym. Sci., Part B: Polym. Phys.,* 25:1071–1078 [1987]).

Concanavalin A (Con A) is a lectin that binds terminal α-D-mannosyl residues (See e.g., Gunther, G. R., "Concanavalin A derivatives with altered biological activities," *Proc. Nat. Acad. Sci.,* USA, 70:1012–1016 [1973]) and has been previously used as a model for the study of mannose-lectin interactions. Similarly, *Triticum Vulgaris* (wheat germ agglutinin "WGA") is a sialic acid (NeuAc)-binding lectin (See e.g., Nagata, Y., and Burger, M. M., "Wheat germ agglutinin: molecular characteristics and specificity for sugar binding," *J. Biol. Chem.,* 249:3116–3122 [1974]). Based on these binding specificities, the series of glycopolythiophenes were examined for their ability to bind and detect these lectins. All of the glycopolythiophene derivatives produced a main absorption peak around 400–430 nm indicating that the degree of conjugation of the polymer backbone is reduced relative to the parent homopolymer (compound 40). The blue-shift of the glycopolymer absorption suggests a more non-planar conformation of the backbone. These relative absorption shifts compared to compound 40, strongly depend on the nature of the substituent in the polymer side chain. This agrees well with previous results that demonstrate the effect of side chain bulk on polymer backbone planarity (See e.g., McCullough, R. D., *Adv. Mater.,* 10:93–116 [1998]).

To demonstrate the biochromic capability of the present inventive glycopolythiophenes, several bioassays were performed. It was hypothesized that, based on previous studies, the degree of planarity in the polymer backbone could depend on electrostatic, H-bonding, steric or van der Waals interactions within or between polymer chains (See e.g., Masella, M. J., and Swager, T. M., *J. Am. Chem. Soc.,* 115:12214–12215 [1993]; Crawford et al., *J. Am. Chem. Soc.,* 120:5187–5192 [1998]; McCullough et al., *J. Am. Chem. Soc.,* 119:633–634 [1997]; Faid, K., and Leclerc, M., *J. Chem. Soc., Chem. Commun.,* 2761–2762 [1996]; Pande et al., *Bioconjugate Chem.,* 7:159–164 [1996]; Charych et al., *Science,* 261:585–588 [1993]; Lee et al., *Synth. Met.,* 69:295–296 [1995]; and Yamamoto et al., "Extensive studies on π-stacking of poly(3-alkylthiophene-2,5-diyl)s and poly(4-alkylthiazole-2,5-diyl)s by optical spectroscopy, NMR analysis, light scattering analysis, and X-ray crystallography," *J. Am. Chem. Soc.,* 120:2047–2058 [1998]). These interactions are expected to be disrupted or altered upon receptor binding.

The steric effects produced by bulky carbohydrates in the glyco-PTs should also be considered (See e.g., Lee et al., *Synth. Met.,* 69:295–296 [1995]; Yamamoto et al., *J. Am. Chem. Soc.,* 120:2047–2058 [1998]). These possible interactions can amplify or reduce the sensing capability of the polymers by planar-nonplanar transitions. Therefore, sialic acid-PTs (series I) and mannose-PTs (series II) were tested to determine the ability of these materials to interact with WGA and Con A, respectively (FIG. 9 and FIG. 10). In the case of series I (FIG. 9), compounds 43, 44 and 49 exhibited a distinct blue-shift of the maximum absorption wavelength upon addition of WGA. The other polymers in this series remained unchanged. This indicates that the carbohydrate-protein interaction occurred, but there is a relatively small change in the conformation of the polymers upon protein addition. Increasing the lectin concentration does not affect the absorption shift. Eventually, the solution precipitated after a few hours. It was expected that polymer compound 47 would be more sensitive than the others due to the extension of the polymer π-conjugation system to the side chain. However, it showed no absorption shift upon addition of WGA.

Similarly, the glyco-PTs of series II were also examined with Con A (FIG. 10). All polymers formed a red-brown precipitate regardless of the concentration of the polymer solution. Indeed, these precipitates were the complexes of mannose-polythiophene and Con A (See e.g., Pagé, D., and Roy, R., "Synthesis of divalent π-D-mannopyranosylated clusters having enriched binding affinities towards concanavalin A and pea lectins," *Bioorg. Med. Chem. Lett.*, 6:7165–1770 [1996]) and precipitation seems to have occurred before the absorption change. This may be due to the higher density of the binding site in Con A (4 subunits per molecule) and also higher its molecular weight (102,000 kDa) than that of WGA (2 subunits/molecule, 36,00 kDa). The Con A effectively cross-links the mannose-PTs before the observation of an absorption shift.

To minimize the problem of precipitation, a biotinylated Con A complexed to streptavidin was used. This complex, when bound to the mannose-PT helps stabilize the polymer-protein complex, presumably by inhibiting cross-linking.

Figure 11:
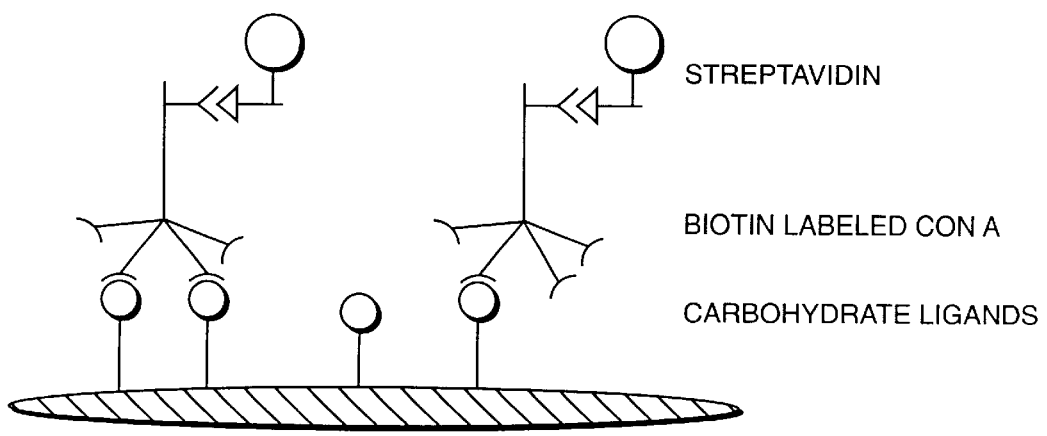
FIG. 11 shows a schematic representation of a double-sandwiched biochromic sensory device based on mannose-PTs.

Using this motif, a small but significant biochromic response was observed upon the addition of streptavidin (FIG. 11). A red-shift of up to 8 nm was observed upon the addition of the protein complex (FIG. 10). The result suggests that the binding of biotin-labelled Con A/streptavidin increases the π-conjugated system of polymer backbone. This result agrees qualitatively with a similar report by Leclerc (Faid, K., and Leclerc, M., *J. Chem. Soc., Chem. Commun.*, 2761–2762 [1996]) where biotin-containing polythiophene was interacted directly with avidin to generate a biochromic response. However, in that report, the protein binding produced a blue-shift of the polymer backbone absorption.

Figure 12:
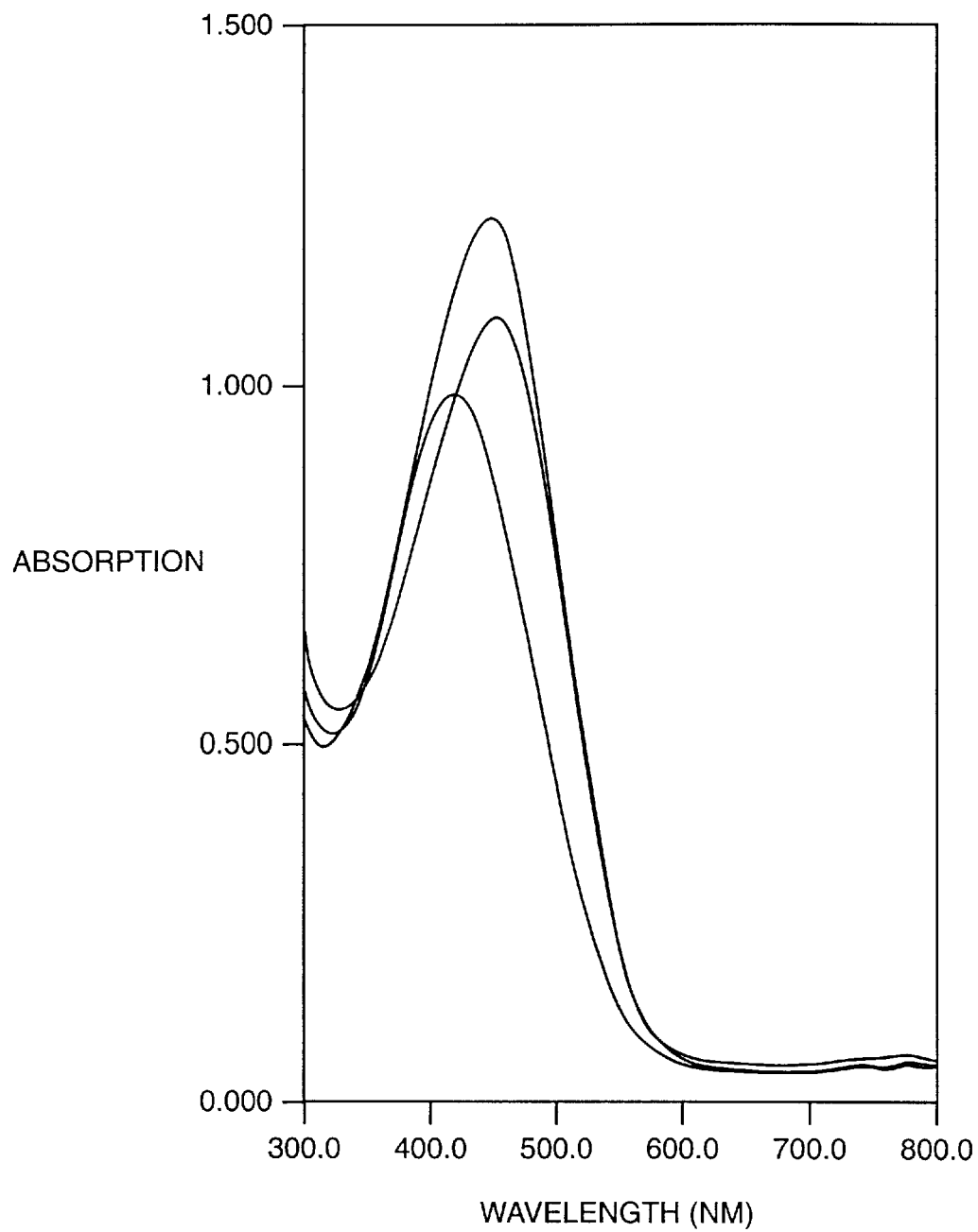
FIG. 12 shows graph of UV-Vis spectroscopic data of reactions of sialic acid-PT (compound 45) before and after addition of influenza virus.
Figure 13:
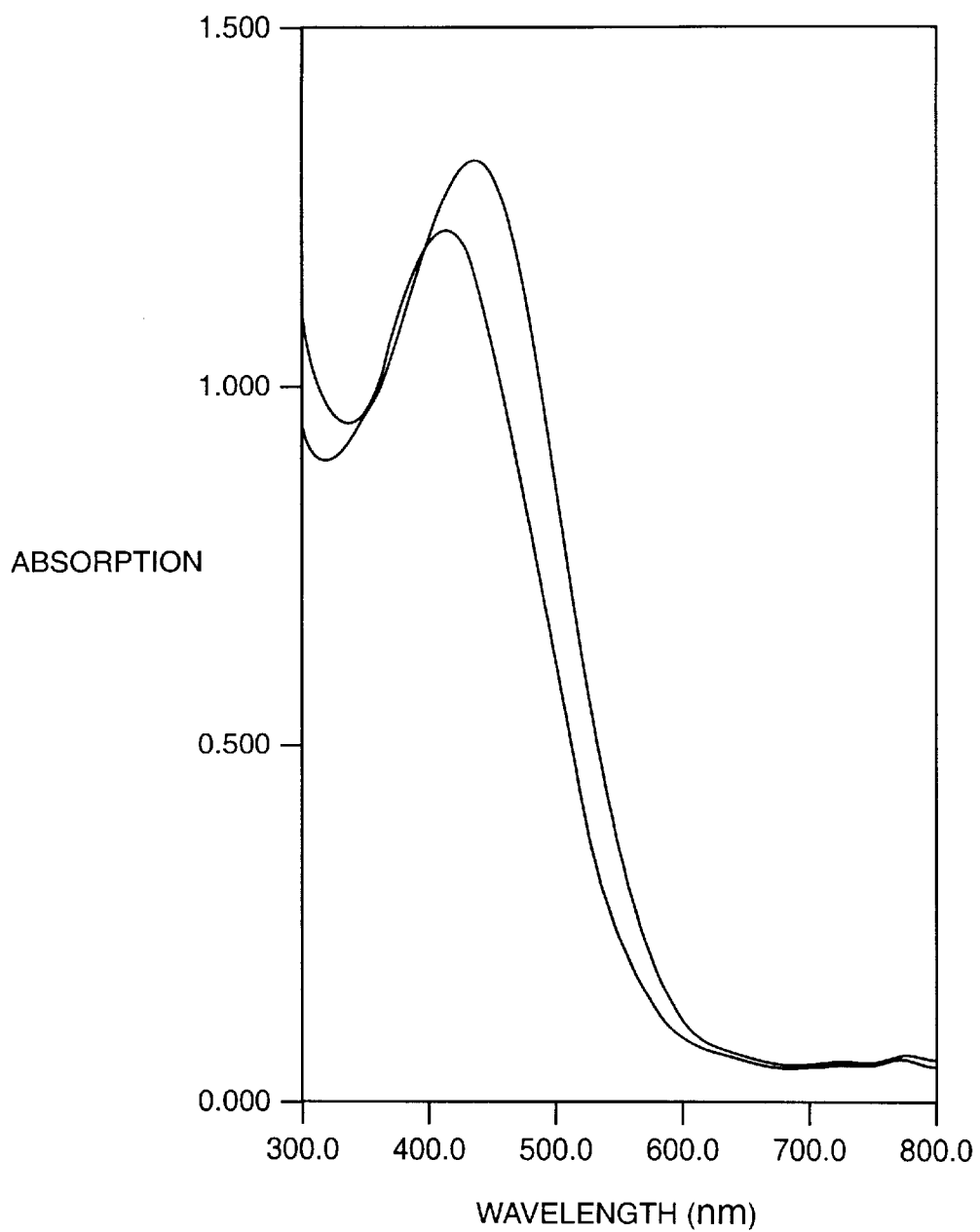
FIG. 13 shows graph of UV-Vis spectroscopic data of reactions of mannose-PT (compound 56) before and after addition of *E. coli*.

Experiments were conducted to determine whether the size and valency of the binding receptor has any influence on the optical shifts observed with these glyco-PTs. To that end, the interactions of influenza virus A and B and *E. coli* (HB101 strain) with the sialic acid-PTs and mannose-PTs, respectively, were investigated. The interaction of these agents with these sugars are documented in the literature (See e.g., Roy et al., *Angew. Chem. Int. Ed. Engl.*, 31:1478–1481 [1992]; Orndorff, P. E., and Falkow, S., *J. Bacteriology*, 160:61–66 [1984]; Old, D. C., *J. Gen. Microb.*, 71:149–157 [1972]; Madison et al., *Infection and Immunology*, 62:843–848 [1994]; Roy et al., *ACS Symposium Series*, 560:104–119 [1993]; Klenk, H. D., and Rott, R., *Advances in Virus Research*, 34:247–281 [1988]; and Pagé, D., and Roy, R., *Bioorg. Med. Chem. Lett.*, 6:7165–1770 [1996]). Surprisingly, all assays indicated an absorption maximum wavelength shift to red in the range of 0 to +27 nm for Influenza virus A, 0 to +32 nm for Influenza virus B and +8 to +32 nm for *E. coli*. For the sialic acid-PTs, polymer compound 45 showed the largest wavelength shift upon addition of both influenza A and B (+27 and +32 nm, respectively) (FIG. 12). For the mannose-PTs, polymer compound 57 showed the largest wavelength shift (+32 nm) after *E. coli* binding (FIG. 13). The wavelength shift was observed with the naked eye, as a color change to dark red. The direction of the wavelength shift is contradictory to those previously reported (See e.g., Faid, K., and Leclerc, M., *J. Chem. Soc., Chem. Commun.*, 2761–2762 [1996]; Pande et al., *Bioconjugate Chem.*, 7:159–164 [1996]; Charych et al., *Science*, 261:585–588 [1993]; and Lio et al., *Langmuir*, 13:6524 [1997]). In the case of the sialic acid-PT series, compounds 41, 42 and 47, having a relatively short side chain showed the weakest wavelength shifts. Moreover, compound 47 exhibited the weakest degree of transition (+4 nm for influenza A, 0 nm for influenza B), most likely because of the inability of the virus to access the carbohydrate on the short linker. This result is similar to that observed using the WGA lectin test (0 nm). The other polymers, compounds 44, 45 and 48 having longer side chains, exhibited $\Delta\lambda_{max}$ values up to 27 nm for influenza A and 32 nm for influenza B, with an observed color change to dark red. Polymer compound 43, which has an intermediate side chain length indicated a wavelength shift of 10 nm.

A similar trend was observed for the mannose-PTs where the absorption maximum shifts were in general, more significant than the sialic acid-PTs. Interestingly, compound 56 showed a strong absorption maximum shift to the red by 25 nm. Similar side chain lengths of compounds 49 and 50 showed somewhat smaller $\Delta\lambda_{max}$ values, +16 and +8 nm, respectively. These results suggest that upon highly cooperative interactions between the carbohydrate and receptor protein, the degree of conjugation of the glycopolythiophene backbone is increased, and the chain is rearranged to a more extended π-conjugated system. In general, the polymers with the longer side chains exhibit greater shift, again suggesting a higher degree of transition to the more planar conformer (see for example, compounds 53–56).

While an understanding of the mechanism of the present invention is not needed, and the present invention is not intended to be limited to any particular mechanism, it is believed that the unusual red-shift of these polymers upon interaction with protein, virus or bacteria, may be explained in a simple sense, by a non-planar to planar transition of the polymer backbone. Because these polymers are soluble polymers in free solution (unlike previous biochromic studies with polydiacetylene where ordered assemblies such as vesicles or LB films were used (See e.g., Pande et al., *Bioconjugate Chem.*, 7:159–164 [1996]; Charych et al., *Science*, 261:585–588 [1993]; and Lio et al., *Langmuir*, 13:6524 [1997])), it is likely that numerous intermolecular interactions can occur. The acidic groups in the polymer backbone and carbohydrate side chains can easily engage in electrostatic or H-bonding interactions. The favorable energetics of these interactions could exceed that of efficient π-orbital overlap of the backbone. Therefore, twisting of the polymer backbone is favored under these conditions. Indeed, these types of interactions are supported by the fact that the homopolymer compound 40, already has an absorption maximum that is significantly more in the red compared all of the carbohydrate-modified polymers (compounds 41–56). Upon binding of the cognate receptor, such as lectin, virus or *E. coli*, the intermolecular interactions between the carbohydrate side chains are disrupted. This would be reasonable since the binding interaction has a higher affinity than the simple intermolecular forces occurring between carbohydrates. Once the intermolecular interactions are disrupted, the polymer assumes a more extended conformation, with decreased twisting of the polymer backbone. The increased π-orbital overlap of this extended conformation results in the observed red shift. In addition, the multivalent nature of the influenza virus and *E. coli* receptors can bind multiple sites on the polymer, further amplifying the changed conformation. This agrees with the greater shifts observed for these particles, in comparison to that of the simple lectins.

IV. Dopants

The biopolymeric materials of the present invention may further comprise one or more dopant materials. Dopants are included to alter and optimize desire properties of the biopolymeric materials. Such properties include, but are not limited to, colorimetric response, color, sensitivity, durability, robustness, amenability to immobilization, temperature sensitivity, and pH sensitivity. Dopant materials include, but are not limited to, lipids, cholesterols, steroids, ergosterols, polyethylene glycols, proteins, peptides, or any other molecule (e.g., surfactants, polysorbate, octoxynol, sodium dodecyl sulfate, zwitterionic detergents, decylglucoside, deoxycholate, diacetylene derivatives, phosphatidylserine, phosphatidylinositol, phosphatidylethanolamine, phosphatidylcholine, phosphatidylglycerol, phosphatidic acid, phosphatidylmethanol, cardiolipin, ceramide, cerebroside, lysophosphatidylcholine, D-erythroshingosine, sphingomyelin, dodecyl phosphocholine, N-biotinyl phosphatidylethanolamine, and other synthetic or natural components of cell membranes) that can be associated with a membrane (e.g., liposomes and films). For example, some embodiments contemplate sialic acid-derived thiophene polymer assemblies comprising ganglioside and thiophene polymers. Such embodiments are contemplated to provide a dramatic increase in colorimetric sensitivity and quantifiability to the detection of low levels of analyte. This improvement in colorimetric response using dopant is extremely beneficial when un-doped materials produce only weak signals. Such is often the case when the ligands are not linked to the polymers (e.g., ganglioside ligands).

In some embodiments, dopants are added to alter the color of the biopolymeric material. For example, the present invention provides compositions that change from blue to red upon introduction to analyte, but also blue to orange, purple to red, purple to orange, green to red, yellow to red, light red to draker red, and green to orange. The advantage with the multi-color approach is that sensors can be made where a specific target turns the material a specific color.

In other embodiments, different dopant materials can be combined in a single biopolymeric material preparation. For example, the present invention comprises a dopant cocktail that is a mix of glucose and sialic acid-derived polydiacetylene. The glucose component of the dopant mixture appears to act primarily to prevent non-specific adhesion to the surface of the inventive liposome and may also enhance sensitivity. The polymer bound sialic acid component appears to functionally destabilize the surface to provide a dramatic increase in sensitivity. By using this co-dopant approach, both specificity of adhesion and sensitivity can be optimized, without unduly compromising the structural integrity of the biopolymeric material.

Although it is not necessary to understand the mechanism in order to use the present invention, and it is not intended that the present invention be so limited, it is contemplated that the addition of dopant lowers the activation barrier of the chromatic transition and/or provides a connection between the ligands (i.e., if ligands are present) and the conjugated backbone, enabling the analyte to induce the colorimetric transition. One theory elucidated during the development of the present invention is that dopants with bulky headgroups (e.g., sialic acid-derived lipid monomers) are subject to various solvent interactions at the matrix surface, destabilizing the structure of the blue film and thus allowing relatively small perturbations provided by the detected analyte (e.g., toxin) to complete the colorimetric transition. Another possible explanation for the improved colorimetric response observed using dopants with bulky headgroups is that the stearic effects induced by the molecular recognition event (i.e., the interaction of the analyte with the biopolymeric material) may interfere with the headgroups of the dopants, thus propagating the perturbation caused by the analyte.

In certain embodiments of the present invention, the dopant comprises a glycopolythiophene or a modified glycopolythiophene (e.g., sialic acid derived glycopolythiophene). It should be noted that in this case, the derivatized polymer is used to modify the properties of the biopolymeric material and is not used as a molecular recognition site for an analyte detection (e.g., as in the case of sialic acid ligand used to detect influenza virus). In some preferred embodiments, neither the ligand, dopant, or matrix is a lipid.

It is contemplated that a wide variety of dopant materials will find use in optimizing the properties of the biopolymeric material used in various embodiments of the present invention. Materials that are constituents of cell membrane structures in nature are generally useful as dopants in the present invention. For instance, steroids (e.g., cholesterols) represent potential dopants that can provide desired degrees of destabilization or stabilization to the biopolymeric material. Surfactant type compounds also may serve as dopants, whether or not they are polymerized to self-assembling monomers that make up the polymer back bone. An alternative surfactant that can be used as dopants are peptide-detergents (i.e., small amphipathic molecules that have a hydrophobic region mimicking the membrane spanning regions of membrane proteins). These small peptides (typically 20–25 amino acids in length) can be incorporated into the biopolymeric material to alter the stability or sensitivity of the colorimetric response of the material when exposed to specific analytes. Since peptide-detergents are bulkier in the hydrophobic region of the material, they are capable of producing a more pronounced effect on film stability or sensitivity than many other surfactant molecules.

The most appropriate percentage of dopant incorporated into the structure of the biopolymeric material is dependent on the particular analytic system being developed, and the needs of the testing situation. For instance, sensitivity may be compromised to some extent in the favor of long shelf life, or to accommodate rigorous field conditions. The acceptable percentage of dopant is theoretically limited only to that which will not preclude sufficient incorporation of the indicator polydiacetylene molecules to produce the necessary optical density and color change or to that which will disrupt the stability of the polymeric structures.

Molar percentages of dopant can vary from as low as 0.01% where increases of sensitivity have been observed in certain embodiments, to as high as 75%, after which the structural integrity of the biopolymeric material typically begins to deteriorate. However, there may be specific embodiments where the percentage of dopant is greater than 75% or lower than 0.01%. A preferred range for dopant is 2%–10%. In certain embodiments of the present invention, the optimal percentage of dopant is about 5%.

In selecting appropriate incorporation methods for the dopant, there are several competing considerations. For example, for the sonication bath method for production of certain liposome embodiments, the incorporation is very controlled, and requires several hours of processing. This relatively slow, gentle incorporation method allows the incorporation of comparatively large or complex dopant materials. However, the sonication bath approach is only suitable when it is intended that a relatively low percentage of dopant is to be incorporated. The point probe method allows the incorporation of a much higher percentage of dopant material over a shorter period of time, typically from one to ten minutes. However, this method is typically limited to incorporation of small to intermediate sized dopant materials. The temperature chosen for incorporation are selected based on the particular analytical system and polymer parameters desired. A practitioner will be able to select parameters such as pH, choice of diluents, and other factors based on the particular system and desired characteristics of the biopolymeric material.

V. Ligands

The biopolymeric materials of the present invention may further comprise one or more ligands. Ligands can act as the recognition site in the biopolymeric materials for analytes. Upon the interaction of the analyte with the ligand or ligands, a disruption of the polymer backbone of the biopolymeric material occurs, resulting in a detectable color transition. Ligands can be linked by a linking arm to the glycopolythiophene, polythiophene, or thiophene monomers, directly linked to the monomers, incorporated into the biopolymeric matrix prior to or during the polymerization process, or attached to the matrix following polymerization (e.g., by linking ligands to matrix constituents that contain head groups that bind to the ligands or through other means).

The ligand groups of the present invention can be comprised of a wide variety of materials. The main criterion is that the ligand have an affinity for the analyte of choice. Appropriate ligands include, but are not limited to, peptides, carbohydrates, nucleic acids, biotin, drugs, chromophores, antigens, chelating compounds, molecular recognition complexes, ionic groups, polymerizable groups, dinitrophenols, linker groups, electron donor or acceptor groups, hydrophobic groups, hydrophilic groups, antibodies, or any organic molecules that bind to receptors. The biopolymeric material can be composed of combinations of ligand-linked and unlinked monomers to optimize the desired colorimetric response (e.g., 5% ligand-linked dicosadynoic acid [DCDA] and 95% DCDA). Additionally, multiple ligands can be incorporated into a single biopolymeric matrix. As is clear from the broad range of ligands that can be used with the present invention, an extremely diverse group of analytes can be detected.

In some embodiments, the inventive monomers are not associated with ligands, but are directly assembled, polymerized, and used as colorimetric sensors. Such biopolymeric materials can find use in the detection of certain classes of analytes including, but not limited to, volatile organic compounds (VOCs).

In some embodiments, ligands are incorporated to detect a variety of pathogenic organisms including, but not limited to, sialic acid to detect HIV (Wies et al., Nature 333: 426 [1988]), influenza (White et al., Cell 56: 725 [1989]), Chlamydia (Infect. Imm. 57: 2378 [1989]), *Neisseria meningitidis, Streptococcus suis,* Salmonella, mumps, newcastle, and various viruses, including reovirus, Sendai virus, and myxovirus; and 9-OAC sialic acid to detect coronavirus, encephalomyelitis virus, and rotavirus; non-sialic acid glycoproteins to detect cytomegalovirus (Virology 176: 337 [1990]) and measles virus (Virology 172: 386 [1989]); CD4 (Khatzman et al., Nature 312: 763 [1985]), vasoactive intestinal peptide (Sacerdote et al., J. of Neuroscience Research 18: 102 [1987]), and peptide T (Ruff et al., FEBS Letters 211: 17 [1987]) to detect HIV; epidermal growth factor to detect vaccinia (Epstein et al., Nature 318: 663 [1985]); acetylcholine receptor to detect rabies (Lentz et al., Science 215: 182 [1982]); Cd3 complement receptor to detect Epstein-Barr virus (Carel et al., J. Biol. Chem. 265: 12293 [1990]); β-adrenergic receptor to detect reovirus (Co et al., Proc. Natl. Acad. Sci. 82: 1494 [1985]); ICAM-1 (Marlin et al., Nature 344: 70 [1990]), N-CAM, and myelin-associated glycoprotein MAb (Shephey et al., Proc. Natl. Acad. Sci. 85: 7743 [1988]) to detect rhinovirus; polio virus receptor to detect polio virus (Mendelsohn et al., Cell 56: 855 [1989]); fibroblast growth factor receptor to detect herpes virus (Kaner et al., Science 248: 1410 [1990]); oligomannose to detect *Escherichia coli;* ganglioside $G_{M1}$ to detect *Neisseria meningitidis;* and antibodies to detect a broad variety of pathogens (e.g., *Neisseria gonorrhoeae, V. vulnificus, V. parahaemolyticus, V. cholerae,* and *V. alginolyticus*).

One skilled in the art will be able to associate a wide variety of ligand types with the biopolymeric materials of the present invention. Methods of derivatizing lipids with a diverse range of compounds (e.g., carbohydrates, proteins, nucleic acids, and other chemical groups) are well known in the art. The carboxylic acid on the terminal end of lipids can be easily modified to form esters, phosphate esters, amino groups, ammoniums, hydrazines, polyethylene oxides, amides, and many other compounds. These chemical groups provide linking groups for carbohydrates, proteins, nucleic acids, and other chemical groups (e.g., carboxylic acids can be directly linked to proteins by making the activated ester, followed by reaction to free amine groups on a protein to form an amide linkage). Examples of antibodies attached to Langmuir films are known in the art (See e.g., Tronin et al., Langmuir 11: 385 [1995]; and Vikholm et al., Langmuir 12: 3276 [1996]). There are numerous other means to couple materials to membranes, or incorporate materials within a membrane, including for example, coupling of proteins or nucleic acids to polymer membranes (See e.g. Bamford et al. Adv. Mat. 6: 550 [1994]); coupling of proteins to self-assembled organic monolayers (See e.g., Willner et al., Adv. Mat. 5: 912 [1993]), and incorporating proteins into membranes (See e.g., Downer et al., Biosensor and Bioelect. 7: 429 [1992]); among others. Protocols for attaching ligands (e.g., proteins, nucleic acids, and carbohydrates) to the colorimetric materials of the present invention are known in the art.

A. Protein Ligands

The methods of the present invention provide, for the first time, a system to easily attach protein molecules, including antibodies, to the surface of glycopolythiophene polymers thereby providing biopolymeric materials with "protein" ligands. Such ligands include, but are not limited to, peptides, proteins, lipoproteins, glycoproteins, enzymes, receptors, channels, and antibodies. Upon binding an analyte (e.g., enzyme substrate, receptor ligand, antigen, and other protein), a disruption of the polymer backbone of the biopolymeric material occurs, resulting in a detectable color change. The present invention contemplates protein ligands that are incorporated into the biopolymeric material and those chemically associated with the surface of the biopolymeric material (e.g., chemically linked to the surface head group of a monomer in the biopolymeric monomer). For example, when the proteins bind a specific molecule, the proteins undergo a conformational change that induces a color change observed in the polymer assemblies.

Specific applications of the present invention are described below to illustrate the broad applicability of the invention to a range of analyte detection systems and to demonstrate its specificity, and ease of use. Coupling of proteins to colorimetric biosensors for three diverse types of molecular targets (i.e., small molecules, proteins, and bacteria) are illustrated. These examples are intended to merely illustrate the broad applicability of the present invention; it is not intended that the present invention be limited to these particular embodiments.

i. Hexokinase Ligands

For example, it is contemplated that the enzyme hexokinase could attached to the polymer assemblies through amine coupling (although other coupling chemistries also work including, but not limited to thiol and aldehyde linkages) to demonstrate the detection of small molecules with a protein ligand.

As described above, the inventive polymer assemblies are useful in the construction of biosensors due to their unique ability to change color in response to mechanical stress. This color change was exploited in the construction of sensors capable of detecting cholera toxin by Charych et al., Chem. and Biol. 3: 113 [1996]) and influenza virus by Charych et al., Science 261: 585 [1993]). In these two examples, the cell surface receptor for the target pathogen was embedded or synthetically coupled to a polydiacetylene thin film. Both the virus and toxin are large macromolecules that bind to the surface of cells and begin their destructive journey by attempting to merge with or insert into the cell membrane. Although it is not necessary to understand the mechanism in order to use the present invention, and it is not intended that the present invention be so limited, it is contemplated that the mechanical stress provoked by the toxin or virus directly disrupts the polymer film causing the polymer to change colors. This approach to biosensor design is optimal only for the detection of molecules that are able to merge with or insert into the polymer. In some embodiments of the present invention, provide a novel biosensory materials that overcome this limitation by utilizing the ligand induced conformational changes of an enzyme (i.e., hexokinase) associated with the polymer surface. The conformational changes in the protein are coupled to the chromatic polymer backbone. The colorimetric change is induced by the enzyme conformational changes caused by the binding of a small molecule to the enzyme active site (i.e., binding of a sugar substrate to the enzyme receptor).

Hexokinase is a ubiquitous metabolic enzyme that catalyzes the transfer of a phosphoryl group from ATP to glucose to form glucose-6-phosphate (Kosow et al., J. Biol. Chem. 246: 2618 [1971]). It is composed of 457 amino acids ($MW \approx 51,000$), 17 of which are lysine residues located on the outside surface of the protein molecule.

Upon binding glucose (MW 180 g/mol), the enzyme undergoes a conformation change (See e.g., Bennett et al., Proc. Natl. Acad. Sci. 75: 4848 [1978]). Coupling the conformational change of the enzyme to the chromatic unit of the polymer assembly could be achieved through protein amine coupling or by other routes.

ii. Antibody Ligands

In addition to the contemplated hexokinase embodiment, the present invention contemplates other protein ligand embodiments, including those specifically designed for antibody-antigen recognition. In these embodiments, polyclonal or monoclonal antibodies are coupled to the polymer assemblies. When the target antigen bound, the antibodies recognize different epitopes on the antigen surface. The stress caused by the binding of these different antibodies to different epitopes is sufficient to induce a conformational color change. The present invention contemplates two examples of such systems: the alpha-factor receptor (i.e., a G-protein coupled receptor) and a sensor for *Chlamydia trachomatis* (i.e., the causative agent of a common STD). The attachment of antibodies to the inventive biopolymeric material provides a colorimetric detection system for an enormous range of analytes (i.e., any analyte for which an antibody can be generated).

Alpha factor receptor antibodies could be used to investigate the general procedure of immobilizing protein onto the monolayer and liposome surface to make immunochemical materials. For example, alpha-factor receptor antibodies could be immobilized to the polymer assemblies through an amide linkage.

A second potential system contemplates the colorimetric detection of the *Chlamydia trachomatis*. Polyclonal antibodies directed against the organism are obtained and immobilized onto the polymer assembly surfaces via a similar method described above for antibody attachment through amine coupling. In this case, the target antigen is present on a bacteria (i.e., a much larger entity than the small molecule or protein antigens used previously). Upon exposing these materials to the analyte (i.e., to the bacteria) a color change will be detected.

Although it is not necessary to understand the mechanism in order to use the present invention, and it is not intended that the present invention be so limited, it is contemplated that with the toxin/virus sensors, the molecules directly interact with the membrane and in the hexokinase system, and that a gross conformational change occurs upon ligand binding. In both of these cases, large conformational changes occur at the membrane surface. With the contemplated antibody approach, the primary driving force for color change is likely the molecule recognition of the antibody-antigen binding event.

VI. Detection of Analytes

The biopolymeric materials of the present invention can be used to detect a large variety of analytes including, but not limited to, small molecules, microorganisms, membrane receptors, membrane fragments, volatile organic compounds (VOCs), enzymes, drugs, antibodies, and other relevant materials by the observation of color changes that occur upon analyte binding. The present invention works under very mild testing conditions, providing the ability to detect small biomolecules in a near natural state and avoiding the risks associated with modification or degradation of the analyte.

In preferred embodiments of the present invention, a color shift was observed simply by visual observation. Thus, the present invention may be easily used by an untrained observer such as an at-home user.

In alternative embodiments, spectral test equipment well known in the art is employed to detect changes in spectral qualities beyond the limits of simple visual observation, including optical density to a particular illuminating light wavelength. For example, using a spectrometer, the spectrum of the material was measured before and after analyte introduction, and the colorimetric response (% CR) is measured. The visible absorption spectrum of the material prior to analyte exposure was measured as $B_o = I_x/(I_y + I_x)$ where "B" represents the percentage of a given color phase at wavelength $I_x$ compared to a reference wavelength $I_y$. The spectrum is then taken following analyte exposure and a similar calculation is made to determine the $B_{final}$. The colorimetric response is calculated as % $CR = [(B_o - B_{final})/B_o] \times 100\%$.

Additionally, some embodiments of the present invention, if desired, can be attached to a transducer device. The association of monomer materials with transducers has been described using optical fibers (See e.g., Beswick and Pitt, J. Colloid Interface Sci. 124: 146 [1988]; and Zhao and Reichert, Langmuir 8: 2785 [1992]), quartz oscillators (See e.g., Furuki and Pu, Thin Solid Films 210: 471 [1992]; and Kepley et al., Anal. Chem. 64: 3191 [1992]), and electrode surfaces (See e.g., Miyasaka et al., Chem. Lett., p. 627 [1990]; and Bilewicz and Majda, Langmuir 7: 2794 [1991]). However, unlike these examples, the present invention provides a double-check (i.e., confirmation method) by observation of color change in the material.

Sensitivity can also be enhanced by coupling the polymers to a photoelectric device, colorimeter, or fiber optic tip that can read at two or more specific wavelengths. Also, the device can be linked to an alternative signalling device such as a sounding alarm or vibration to provide simple interpretation of the signal.

VII. Immobilization of Biopolymeric Materials

In preferred embodiments of the present invention, the inventive compositions comprise soluble polymer systems and assemblies. Moreover, in some embodiments of the present invention, the biopolymeric materials can be immobilized on a variety of solid supports, including, but not limited to polystyrene, polyethylene, teflon, silica gel beads, hydrophobized silica, mica, filter paper (e.g., nylon, cellulose, and nitrocellulose), glass beads and slides, gold and all separation media such as silica gel, sephadex, and other chromatographic media. In some preferred embodiments, the biopolymeric materials are immobilized in silica glass using the sol-gel process. In some other particularly preferred embodiments, the soluble polymer systems are contained in wells, vials, troughs, tubes, and the like. In some embodiments, immobilizing supports, including wells, troughs, tubes, and the like, are functionalized with one or more additional molecules. For example, in some embodiments where the soluble polymers systems are placed in wells, the surfaces of the wells are functionalized with immobilized antibodies.

Immobilization of the colorimetric biopolymeric materials of the present invention may be desired to improve their stability, robustness, shelf-life, colorimetric response, color, ease of use, assembly into devices (e.g., arrays), and other desired properties. In some embodiments, placement of colorimetric materials onto a variety of substrates surfaces can be undertaken to create a test method similar to the well-known and easy to use litmus paper test. For example, the reflective properties of nylon filter paper greatly enhance the colorimetric properties of the immobilized polydiacetylene liposomes. Filter paper also increases the stability of the polymer assemblies due to the mesh size. In another example, an embodiment of the present invention is loaded into the ink cartridge of a ink jet printer and used to print biopolymeric material onto paper as though it were ink. It is contemplated that polymer assemblies present on the paper will maintain their colorimetric properties.

In some embodiments of the present invention, the biopolymeric material can be attached to membranes of poly(ether urethanes) or polyacrylonitrile. These membranes are porous, hydrophilic and can be used for affinity separations or immunodiagnosis.

A variety of other immobilization techniques known in the art can be applied to the biopolymeric materials of the present invention. For example, materials which have an —SH functionality can be immobilized directly to gold surfaces, particles, or electrodes via a thiol-gold bond. It is also contemplated that the inventive materials can be immobilized to silicon chips or silica gel (e.g., silicon dioxide) using the procedure known in the art. Furthermore, materials containing —$NH_2$ functionalities can also be immobilized onto surfaces with standard glutaraldehyde coupling reactions that are often used with the immobilization of proteins.

VIII. Arrays

Certain embodiments of the present invention contemplate the generation of a large palette of polymerizable monomers with different headgroup chemistries, ligands, dopants, monomers or other properties within a single device to increase selectivity, sensitivity, quantitation, ease of use, portability, among other desired characteristics and qualities. By using the array format, several advantages can be realized that overcome the shortcomings of a single sensor approach. These include the ability to use partially selective sensors and to measure multicomponent samples. This offers the possibility of sensing a specific analyte in the presence of an interfering background, or to monitor two or more analytes of interest at the same time. The sensitivities of a given lipid to a given solvent can be determined in order to generate identifiable fingerprints characteristic of each solvent.

Clearly, the higher the number of elements in the array, the greater the chance of a positive identification for a given analyte. By immobilizing the biopolymeric material, materials of any desired size and shape can be created and incorporated into a small, easily read and interpretable device.

Experimental

The following examples are provided in order to demonstrate and further illustrate certain preferred embodiments and aspects of the present invention and are not to be construed as limiting the scope thereof.

In the experimental disclosure which follows, the following abbreviations apply: N (normal); M (molar); mM (millimolar); $\mu$M (micromolar); mol (moles); mmol (millimoles); $\mu$mol (micromoles); nmol (nanomoles); pmol (picomoles); g (grams); mg (milligrams); $\mu$g (micrograms); ng (nanograms); l or L (liters); ml (milliliters); $\mu$l (microliters); cm (centimeters); mm (millimeters); $\mu$m (micrometers); nm (nanometers); and °C. (degrees Centigrade).

EXAMPLE 1

General Procedures

This example describes general procedures used during the development of the present invention. Air and moisture sensitive reactions were carried out in dried glassware under nitrogen atmosphere. Chloroform was distilled from phosphorus pentoxide. Methanol was degassed by technique of melt and thaw under high vacuum condition until no gas bubbles were observed and handled under nitrogen prior to use. Sialic acid and p-nitrophenyl mannopyranoside were obtained from Rose Scientific Ltd (Edmonton, Canada). 3-thiopheneacetic acid was obtained from Acros Organics (Fisher Scientific, Pittsburgh, Pa.). *Triticum Vulgaris* (Wheat germ), Concanavalin A (Con A), biotin labeled Con A (Sigma, St. Louis, Mo.) and streptavidin (Pierce, Rockford, Ill.) were used as received. Influenza virus was obtained from Department of Health Service, Public Health Laboratory, San Diego. *E. Coli* (HB101) was obtained from department of Plant and Microbial Biology, UC Berkeley. All other reagents were used as received from Aldrich (St. Louis, Mo.). NMR spectra were recorded with a Bruker AMX-300 (300 MHz), VBAM-400 (400 MHz) or AMX-500 (500 MHz) Spectrometer (Madison, Wis.). Optical rotations were recorded with a Perkin Elmer Polarimeter model 241 (Santa Clara, Calif.). UV-vis absorption spectroscopy was performed on Shimadzu (Columbia, Md.) Spectrophotometer (model UV-1601).

EXAMPLE 2

Polymerization

This example describes the various polymerization routines employed in the present invention.

Oxidative polymerization by $FeCl_3$. To a suspension of $FeCl_3$ (4 equiv) in dry $CHCl_3$ (5 mL) was saturated with $N_2$ and a solution of sugar-thiopene monomer and methyl-3- thiopheneacetate (mole ratio, 1/5) mixture in dry $CHCl_3$ (6 mL) was added dropwise over 2 h period. The mixture was stirred for 3 days at room temperature. The solution was precipitated into MeOH (20 mL), and the brownish solid was collected, washed with MeOH. Polymers were subsequently washed by Soxhlet extraction using MeOH and the residue was dried under reduced pressure to give redbrownish solid. (for sialic acid glycopolymers; 31~50% (w/w), for mannose glycopolymers; 28–46% (w/w)).

Graft conjugation of carbohydrates by peptide coupling. TBTU (1.2 eq.) and DIPEA were added to a solution of polythiopheneacetic acid and amine functionalized carbohydrates in DMF. The solution was stirred at an ambient temperature for 5 h. Once complete consumption of the carbohydrate moieties occurred, the solution was condensed to approximately one-third of its volume and then MeOH (10 mL) was added. The solution was stood in the refrigerator for 1 day to induce precipitate. A brown solid was filtered off and this solid was washed successively with MeOH and subsequently dried under reduced pressure to give the desired product.

De-O-acetylation and de-esterification of glycopolymers. Glycopolythiophene-co-methyl ester (0.2 g) was suspended in $CHCl_3$ (10 mL). $CH_3O^-Na^+$/MeOH (25 wt. %) was added to adjust pH to about 9. The solution was stirred at room temperature for 7 h. The solution was dried under reduced pressure, then treated with 0.3 M aqueous NaOH solution (7 mL) for another 5–10 h at room temperature. The insoluble portion was filtered off through a Celite pad and the filtrate was dialyzed (12,000 MW cut-off) against distilled water (2 L) for 3 days. This solution was employed for the assays without further purification.

EXAMPLE 3

Synthesis of Succinimidyl (3-Thienyl)acetate (Compound 9)

This example describes the synthesis of Succinimidyl (3-Thienyl)acetate (compound 9). Thionyl chloride (0.6 mL, 1 eq.) was slowly added at room temperature to a solution of thiophene-3-acetic acid (1 g, 7.8 mmol) in $CHCl_3$ (25 mL). The resulting solution was refluxed at 90° C. for 1 h. After the solution was cooled to room temperature, a mixture of N-hydroxy succinimide (0.9 g, 1 eq.) and DIPEA (2.8 mL, 1 eq.) in $CHCl_3$ (20 mL) was slowly added at ice-water temperature. The solution was then stirred overnight at room temperature. The solution was washed with water then dried over $Na_2SO_4$. The solvent was removed by rotary evaporation and the residue was purified by silica gel column chromatography with $CHCl_3$/MeOH (40/1), or recrystallized with ($CHCl_3$/hexane, 1/1) after flash silica gel column chromatography to afford yellowish powder in 71% yield (1.32 g, 5.5 mmol). MS (EI): 240.0 ($MWH^+$), $^1H$-NMR ($CDCl_3$): $\delta 7.30$ (dd, 1H $^4J=2.96$ HZ, $^4J=4.90$ vHz, thiophene), 7.26 (m, 1H, thiophene), 7.06 (dd, 1H, J=1.32 HZ, $^4J=4.90$ Hz, thiophene), 3.94 (s, 2H, $CH_2$), 2.76 (s, 4H, 2 $CH_2$), $^{13}C$-NMR ($CDCl_3$): $\delta 169.5$, 166.7, 131.1, 128.5 126.6, 124.2, 32.7, 25.9.

EXAMPLE 4

Synthesis of 4-[(3-Thienyl)acetamidolbutanoic acid (Compound 12)

This example describes the synthesis of 4-[3-Thienylacetamido]butanoic acid (compound 12). A couple of drops of DIPEA were added to a solution of thiophene active ester (compound 9) (1.1 g, 4.6 mmol) and 4-aminobutanoic acid (compound 10) (48 g, 4.6 mmol) in $CHCl_3$ (55 ml) the resulting solution was stirred overnight at room temperature. A white precipitate was filtered off and the filtrate was condensed. Without further work-up, the residue was purified by silica gel column chromatography ($CHCl_3$/MeOH, 10/1) to give a white solid (0.7 g, 3.1 mmol) in 67.4% yield. MS (EI): 228.0 ($MH^+$), Mp: 77.3~77.6° C., $^1H$-NMR ($CD_3OD$): $\delta 7.27$ (dd, 1H, J=3.0 Hz, $^4J=4.7$ Hz, thiophene), 7.11 (m, 1H, thiophene), 6.95 (dd, 1H, J=1.1 Hz, $^4J=4.8$ Hz, thiophene), 3.44 (s, 2H, thiophene-$CH_2$), 3.14 (t, 2H, J=6.9 Hz, amide-$CH_2$), 2.22 (t, 2H, J=7.4 Hz, $CH_2$-acid), 1.70 m, 2H, $CH_2$) $^{13}C$-NMR ($CD_3OD$): $\delta 178.2$, 174.0, 136.8, 129.4, 126.9, 123.6, 40.1, 38.6, 32.3, 25.9.

EXAMPLE 5

Synthesis of 6-[(3-Thienyl)acetamido]caproic acid (Compound 13)

This example describes the synthesis of 6-[3-Thienylacetamido]caproic acid (compound 13). A solution of thiophene active ester (compound 9) (0.1 g, 0.42 mmol) and 6-aminocaproic acid (compound 11) (5 mg, 4.2 mmol) in $CHCl_3$ (5 mL) were coupled as described in Example 2 to give a white solid (97 mg, 0.38 mmol) in 90% yield. MS (EI): 255.0 ($M^+$), Mp: 78.6~79.5° C., $^1H$-NMR ($CD_3OD$): $\delta 7.33$ (1H, dd, J=3.0 Hz, $^4J=4.9$ Hz, thiophene), 7.17 (1H, m, thiophene), 7.01 (1H, dd, J=1.1 Hz, $^4J=4.9$ Hz), 3.49 (s, 2H thiophene-$CH_2$), 3.16 (t, 2H, J=6.9 Hz, amide-$CH_2$), 2.25 (t, 2H, J=7.4 Hz, $CH_2$-acid), 1.63~1.42 (m, 4H, 2 $CH_2$), 1.36~1.28 (m, 2H, $CH_2$), $^{13}C$-NMR ($CD_3OD$): $\delta 177.6$, 173.8, 136.9, 129.5, 126.9, 123.6, 40.5, 38.7, 35.0, 30.2, 27.6, 25.9.

EXAMPLE 6

Synthesis of 2-[(3-Thienyl)acetamido]-1-aminoethane (Compound 16)

This example describes the synthesis of 2-[(3-Thienyl)acetamido]-1-aminoethane (compound 16). Thiophene active ester (compound 9) (1.0 g, 4.4 mmol) in $CHCl_3$ (30 mL) was added dropwise at room temperature over a 2 h period to a solution of ethylenediamine (356 µL, 5.3 mmol) in $CHCl_3$ (200 mL). During the addition of the active ester, white precipitate was formed. The mixture was stirred overnight at room temperature. The precipitate was filtered off and the filtrate was extracted with aq. 1 M HCl (30 mL×5). The aqueous layer was combined and evaporated under reduced pressure. The residue was purified by silica gel column chromatography with ($CHCl_3$/MeOH/2-propanol, 5/3/2) to give white hygroscopic solid in 83% yield (3.7 g, 20 mmol). MS (EI): 184 ($M^+$), Mp: 89.7~92.1° C., $^1H$-NMR ($CD_3OD$): $\delta 7.34$ (dd, 1H, thiophene), 7.20 (m, 1H, thiophene), 7.04 (dd, 1H, $^4J=5.0$ Hz, $^4J=1.1$ Hz thiophene), 3.54 (s, 2H, $CH_2$), 3.25 (t, 2H, J=6.3 Hz, $CH_2$), 2.73 (t, 2H, J=6.3 Hz, $CH_2$), $^{13}C$-NMR ($CD_3OD$): $\delta 174.3$, 136.8, 129.5, 126.9, 123.7, 42.9, 42.0, 38.6.

EXAMPLE 7

Synthesis of 8-[(3-Thienyl)acetamido]-1-octylamine (Compound 17)

This example describes the synthesis of 8-[(3-Thienyl] acetamido)-1-octylamine (compound 17). 1,8-Octanediamine (0.78 g, 5.4 mmol) and compound 9 (1.2 g, 1 equiv) were coupled as described in Example 6 to give yellowish resin (1.4 g, 5.2 mmol) in 96% yield. MS (EI): 268 (M$^+$), $^1$H-NMR (CD$_3$OD): δ7.31 (dd, 1H, J=2.9 Hz, $^4$J=4.9 Hz, thiophene), 8.13 (broad s, 1H, thiophene), 6.98 (dd, 1H, J=1.2 Hz, $^4$J=4.9 Hz, thiophene), 3.45 (s, 2H, thiophene-CH$_2$), 3.11 (m, 2H, amide-CH$_2$), 2.82 (m, 2H, CH$_2$-amine), 1.43 (m, 8H, 4 CH$_2$), $^{13}$C-NMR (CD$_3$OD): δ173, 137.0, 129.4, 126.8, 123.6, 40.9, 40.6, 38.7, 30.4, 30.2, 30.1, 28.6, 27.8, 27.5.

EXAMPLE 8

Synthesis of 8-[(3-Thienyl)acrylamido]-1-octylamine (Compound 20)

This example describes the synthesis of 8-[(3-Thienyl) acrylamido]-1-octylamine (compound 20). HOBt (0.7 g, 1.2 equiv) at ice water temperature was added to a solution of compound 18 (1.1 g, 4.4 mmol) and compound 19 (0.7 g, 1 equiv) in CHCl$_3$ (30 mL). The solution was stirred for 15 min, then DIPEA (pH 9) and EDC (1 g, 1.2 equiv) were added. The reaction was continued at room temperature for 6 h. The reaction mixture was then diluted with CHCl$_3$ (30 mL), washed successively with saturated NaHCO$_3$ (aq) and water, and dried over NaSO$_4$. The solution was briefly condensed and the residue was purified by silica gel column chromatography (EtOAc/hexane, 4/1) to give a yellowish solid. Subsequently, the solid was treated with TFA (30% in HC$_2$Cl$_2$) for 3 h at room temperature to give a light yellowish solid in overall 87% yield (1.07 g, 3.8 mmol). Mp: 147.2~147.9° C., $^1$H-NMR (CDCl$_3$): δ7.58 (broad s, thiophene), 7.50 (d, 1H, J$_{trans}$=15.5 Hz, =CH—C(O)NH), 7.42 (m, 1H, J=2.9 Hz, $^4$J=5.0 Hz, thiophene), 7.33 (broad d, 1H, thiophene), 6.42 (d, 1H, thiophene-CH=), 3.26 (t, 2H, J=7.2 Hz, CH$_2$), 2.88 (t, 2H, J=7.7 Hz, CH$_2$), 1.62 (m, 2H, CH$_2$), 1.53 (m, 2H, CH$_2$), 1.35 (m, 6H, CH$_2$), $^{13}$C-NMR (CDCl$_3$): δ183.3, 167.5, 137.9, 126.9, 126.6, 124.7, 133.9, 120.1, 39.3, 39.1, 29.0, 28.7, 27.1, 26.5, 25.9.

EXAMPLE 9

Synthesis of p-[(3-Thienyl)acetamido]acetamido] phenyl Methyl (5-Aceta-mido-4,7,8,9-tetra-O-acetyl-3,5-dideoxy-D-glycero-α-D-glacto-2-nonulopyranosid)onate (Compound 21)

This example describes the synthesis of p-[(3-Thienyl) acetamido]acetamido]phenyl Methyl (5-Aceta-mido-4,7,8,9-tetra-O-acetyl-3,5-dideoxy-D-glycero-α-D-glacto-2-nonulopyranosid)onate (compound 21). DIPEA (pH=9) and TBTU (0.27 g, 1.2 equiv) were added to a solution of compound 1 (0.4 g, 0.7 mmol) and thiopheneacetic acid (0.90 mg, 1 equiv) in CH$_2$Cl$_2$ (5 mL). The resulting solution was stirred at an ambient temperature for 5 h. The solution was diluted with CH$_2$Cl$_2$ (10 mL) and washed successively with saturated NaHCO$_3$ and water, then dried over Na$_2$SO4. The solvent was evaporated by rotary evaporator. The residue was purified by silica gel column chromatography (CHCl$_3$/MeOH, 10/1) to give ivory foam solid (0.43 g, 0.62 mmol) in 90% yield. MS (positive FAB): 707.3 (MH$^+$), [α]$_D$: +15° (c, 2.0, MeOH), Mp: 58.5~60.7° C., $^1$H-NMR (CDCl$_3$): δ8.33 (s, 1H, NH), 7.33 (d, 2H, J$_{om}$=8.6 Hz, aromatic-ortho), 7.23 (dd, 1H, J=2.8 HZ, $^4$J=4.9 Hz, thiophene), 7.12 (broad s, 1H, thiophene), 6.98 (dd, 1H, J=1.2 Hz, $^4$J=4.9 Hz, thiophene), 6.91 (d, 2H, aromatic-meta), 6.41 (d, 1H, J$_{N5}$=9.8 Hz, NH), 5.31 (m, 2H, H-7, H-8), 4.85 (ddd, 1H, J$_{45}$=10.2 Hz, J$_{43e}$=4.7 Hz, J$_{43a}$=11.7 Hz, H-4), 4.31 (dd, 1H, J$_{56}$=10.7 Hz, H-6), 4.21 (dd, 1H, J$_{9a9b}$=10.3 Hz, H-9a), 4.06 (m, 2H, H-5, H-9b), 3.63 (s, 3H, C(O)O—CH$_3$), 3.51 (s, 2H, CH$_2$-thiophene), 2.64 (dd, J$_{3e4}$= 4.4 Hz, J$_{3e3a}$=12.9 Hz, H-3e), 2.10 (dd, 1H, J$_{3a4}$=11.2 Hz, H-3a), 2.02, 2.01, 1.93, 1.92, 1.79 (5 s, 15H, 5 AcO), $^{13}$C-NMR (CDCl$_3$): δ171.0, 170.9, 170.4, 170.3, 169.3, 168.2, 150.2, 135.0, 134.7, 128.8, 126.7, 123.5, 121.2, 120.9, 100.5, 73.5, 69.4, 69.3, 67.6, 62.3, 53.1, 49.2, 39.1, 38.8, 23.3, 21.2, 21.0.

EXAMPLE 10

Synthesis of Compound 22

This example describes the synthesis of compound 22. Compound 22 was prepared from compound 1 and compound 12 using the peptide coupling protocol. Yield: 75%; FAB (+) –MS: 791.3 (MH$^+$), [α]$_D$: +17° (c, 1.8, MeOH), $^1$H-NMR (CDCl$_3$): 6.28 (t, 1H, J$_{NCH2}$=5.6 Hz, NH), 5.85 (d, 1H, J$_{N5}$=9.9 Hz, NH), 3.28 (m, 2H, CH$_2$—HNC(O)), 2.29 (t, 2H, J=6.0 Hz, HNC(O)—CH$_2$), 1.78 (m, 2H, CH$_2$), $^{13}$C-NMR (CDCl$_3$): 39.3, 38.3, 34.9, 28.9. Other chemical shifts are the same as for compound 21.

EXAMPLE 11

Synthesis of Compound 23

This example describes the synthesis of compound 23. Compound 23 was prepared from compound 1 and compound 13 using the peptide coupling protocol. Yield: 86%; MS (positive FAB): 820.3 (MH$^+$), [α]$_D$: +13° (c, 1.0, MeOH), Mp: 71~73° C. $^1$H-NMR (CDCl$_3$): δ6.18 (t, 1H, J$_{NCH2}$=5.7 Hz, NH), 6.12 (d, 1H, J$_{N5}$=9.9 Hz, NH), 3.11 (m, 2H, CH$_2$—HNC(O)), 2.22 (m, 2H, HNC(O)—CH$_2$), 1.58 (m, 2H, CH$_2$), 1.39 (m, 2H, CH$_2$), 1.24 (m, 2H, CH$_2$), $^{13}$C-NMR (CDCl$_3$): δ39.3, 36.9, 28.9, 27.8, 26.1. Other chemical shifts are the same as for compound 21.

EXAMPLE 12

Synthesis of Compound 24

This example describes the synthesis of compound 24. Compound 24 was prepared from compound 3 and compound 13 using the peptide coupling protocol. Yield 60%; MS (positive FAB): 951.5 (MH$^+$), Mp: 76~77° C., [α]$_D$: +2.4° (c, 1.7, MeOH), $^1$H-NMR (CDCl$_3$): δ8.61 (s, 1H, NH), 7.99 (s, 1H, NH), 7.47 (d, 2H, J$_{om}$=8.9 Hz, aromatic-ortho), 7.31 (dd, 1H, $^4$J=4.9 HZ, $^4$J=4.9 Hz, thiophene), 7.12 (m, 1H, thiophene), 6.98 (m, 3H, aromatic-meta, thiophene), 6.29 (m, 1H, NH), 5.81 (m, 1H, NH), 5.34 (broad s, 1H, H-7, H-8), 4.92 (ddd, 1H, J$_{45}$=10.2 Hz, J$_{43c}$=4.7 Hz, J$_{43a}$=11.7 Hz, H-4), 4.33 (m, 2H, H-6, H-9), 4.11 (m, 2H, H-5, H-9b), 3.63 (s, 3H, C(O)O—CH$_3$), 3.57 (s, 2H, CH$_2$-thiophene), 3.42 (m, 2H, CH$_2$), 3.19 (m, 2H, CH$_2$), 2.89 (t, 2H, hidden, CH$_2$), 2.65 (m, 7H, H-3e, 3 CH$_2$), 2.15 (dd, 1H, J$_{3a4}$=11.2 Hz, J$_{3a4}$=9.4 Hz, H-3a), 2.10, 2.09, 2.02, 2.01, 1.88 (5 s, 15H, 5 AcO), 1.58 (m, 2H, CH$_2$), 1.41 (m, 2H, CH$_2$), 1.25 (m, 2H, CH$_2$), $^{13}$C-NMR (CDCl$_3$): δ176.9, 173.3, 170.9, 170.3, 170.0, 167.9, 162.6, 149.8, 134.9, 134.8, 128.5, 126.7, 120.8, 123.4, 120.7, 100.3, 73.3, 69.3, 68.9, 67.4, 62.0, 52.9, 49.4, 37.9, 39.4, 38.5, 38.1, 37.4, 36.5, 16.3, 31.9, 31.4, 29.1, 27.3, 26.1, 25.1, 23.2, 21.0, 20.8.

EXAMPLE 13

Synthesis of Compound 25

This example describes the synthesis of compound 25. Compound 25 was prepared from compound 1 and compound 19 using the peptide coupling protocol. Yield: 82%; MS (positive FAB): 719.2 (MH$^+$), [α]$_D$: +17° (c, 1.4, MeOH), Mp: 79.3~81.1° C. $^1$H-NMR (CDCl$_3$): δ7.62 (d, 1H, J$_{trans}$=15.5 Hz, HNC(O)CH=), 6.51 (m, 2H, =CH-thiophene, NH), 5.34 (m, 2H, H-7, H-8), 4.88 (ddd, 1H, J$_{45}$=10.2 Hz, J$_{3e-4}$=4.7 Hz, J$_{3a-4}$=11.7 Hz, H-4), 4.34 (dd, 1H, J$_{56}$=10.5 Hz, H-6), 4.24 (dd, 1H, J$_{9ab}$=12.4 Hz, H-9a), 4.06 (m, 2H, H-9b, H-5), 3.51 (s, 3H, CO$_2$CH$_3$), 2.50 (hidden, 1H, H-3e), 2.13 (hidden, 1H, H-3a), (5 s, 15H, AcO), $^{13}$C-NMR (CDCl$_3$): 5 171.1, 170.9, 170.4, 170.3, 168.2, 166.0, 151.2, 138.2, 135.5, 127.7, 127.1, 125.5, 121.0, 100.6, 73.5, 69.4, 67.7, 62.3, 53.1, 49.2, 38.3, 23.2, 21.2, 21.1.

EXAMPLE 14

Synthesis of p-[(3-Thienyl)acetamido]phenyl-α-D-2,3,4,6-tetra-O-acetyl mannopyranoside (Compound 26)

This example describes the synthesis of compound 26. DIPEA (0.8 mL) and TBTU (1.8 g, 5.5 mmol) were added to a solution of 4-aminophenyl-α-D-mannopyranoside (compound 4) (2.0 g, 4.6 mmol) and thiopheneacetic acid (compound 6) (0.6 g, 4.6 mmol) in CH$_2$Cl$_2$ (50 ml). The resulting solution was stirred for 4 h at room temperature. The solution was diluted with CH$_2$Cl$_2$ (20 mL) and washed with saturated aqueous NaHCO$_3$ (aq) and water then dried over Na$_2$SO$_4$. The solution was dried under reduced pressure and the crude product was purified by silica gel column chromatography with EtOAc/Hex (2/1) to give light yellowish amorphous solid in 83% yield (0.21 g, 0.38 mmol). MS (positive FAB): 564 (MH$^+$), 586.3 (MNa$^+$), [α]$_D$: +47.9° (c, 1.4, CHCl$_3$), MP: 62.5~64.0° C., $^1$H-NMR (CDCl$_3$): δ7.35 (m, 3H, aromatic-ortho, thiophene), 7.19 (m, 1H, thiophene), 7.03 (d, 1H, J=4.9 Hz, thiophene), 6.98 (d, 2H, J$_{om}$=9.0 Hz, aromatic-meta), 5.50 (dd, 1H, J$_{23}$=3.4 Hz, J$_{34}$=10.0 Hz, H-3), 5.41 (d, 1H, J$_{12}$=1.9 Hz, H-1), 5.39 (dd, 1H, J$_{23}$=3.3 Hz, H-2), 5.34 (dd, 1H, J$_{34}$=10.0 Hz, J$_{45}$≦1 Hz, H-4), 4.24 (dd, 1H, J$_{5-6a}$=5.4 Hz, J$_{6-6a}$=12.4 Hz, H-6a), 4.04 (m, 2H, H-5, H-6b), 3.71 (s, 2H, CH$_2$), 2.16, 2.02, 2.01, 2.00 (4 s, 4 AcO), $^{13}$C-NMR (CDCl$_3$): δ176.0, 170.6, 170.0, 169.7, 168.7, 134.4, 133.0, 128.4, 127.0, 123.7, 121.5, 117.0, 96.1, 69.3, 69.1, 68.9, 65.9, 62.1, 38.9, 20.9, 20.8, 20.7.

EXAMPLE 15

Synthesis of Compound 27

This example describes the synthesis of compound 27. Compound 27 was prepared from compound 4 and compound 12 using the peptide coupling protocol. Yield (quantitative); MS (positive FAB): 649 (NH$^{30}$ ), [α]$_D$: +45.5° (c, 3.3, CHCl$_3$), $^1$H-NMR (CDCl$_3$): δ9.04 (broad s, 1H, NH), 7.50 (d, 2H, J$_{om}$=9.1 Hz, aromatic-ortho), 7.28 (dd, 1H, J=3.0 Hz, $^4$J=4.9 Hz, thiophene), 7.09 (broad s, 1H, thiophene), 6.96 (m, 3H, aromatic-meta, thiophene), 6.25 (broad t, 1H, NH), 5.51 (dd, 1H, J$_{23}$=8.4 Hz, J$_{34}$=10.0 Hz, H-3), 5.43 (d, 1H, J$_{12}$=1.9 Hz, H-1), 5.40 (dd, 1H, J$_{23}$=3.5 Hz, H-2), 5.32 (dd, 1H, J$_{34}$=10.0 Hz, J$_{45}$≦1 Hz, H-4), 4.24 (dd, 1H, J$_{56a}$=5.0 Hz, J$_{6ab}$=12.1 Hz, H-6a), 4.08~4.00 (m, 2H, H-5, H-6b), 3.56 (s, 2H, thiophene-CH$_2$), 3.28 (m, 2H, CH$_2$-amide), 2.28 (m, 2H, carbonyl-CH$_2$), 2.16, 2.01, 2.00, 1.99 (4 AcO), 1.79 (m, 2H, CH$_2$) $^{13}$C-NMR (CDCl$_3$): δ171.9, 171.1, 170.6, 170.0, 169.9, 169.7, 156.0, 134.6, 133.9, 128.4, 126.7, 123.5, 121.2, 116.9, 96.1, 69.4, 69.1, 68.9, 65.9, 62.1, 38.9, 38.6, 38.1, 34.5, 26.2, 20.9, 20.7.

EXAMPLE 16

Synthesis of Compound 28

This example describes the synthesis of compound 28. Compound 28 was prepared from compound 4 and compound 13 using the peptide coupling protocol. Yield (quantitative); MS (positive FAB): 677 (MH$^+$), [α]$_D$: +39.2° (c, 2.6, MeOH), $^1$H-NMR (CDCl$_3$): δ7.95 (:broad s, 1H, NH), 7.45 (d, 2H, J$_{om}$=9.0 Hz, aromatic-ortho), 7.28 (dd, 1H, J=2.9 Hz, $^4$J=4.9 Hz, thiophene), 7.01 (broad s, 1H, thiophene), 6.96 (d, 2H, aromatic-meta), 6.94 (dd, 1H, J=1.2 Hz, $^4$J=4.9 Hz, thiophene), 5.78 (broad t, 1H, NH), 5.51 (dd, 1H, J$_{23}$=3.4 Hz, J$_{34}$=10.0 Hz, H-3), 5.40 (m, 2H, H-1, H-2), 5.33 (dd, 1H, J$_{34}$=10 Hz, J$_{45}$≦1, H-4), 4.24 (dd, 1H, J$_{56a}$=4.8 Hz, J$_{6ab}$=11.9 Hz, H-6a), 4.05 (m, 2H, H-5, H-6b), 3.54 (s, 2H, thiophene-CH$_2$), 3.18 (m, 2H, CH$_2$-amide), 2.26 (m, 2H, C(O)—CH$_2$), 2.16, 2.02, 2.01, 2.00 (4 AcO), 1.66 (m, 2H, CH$_2$), 1.45 (m, 2H, CH$_2$), 1.28 (m, 2H, CH$_2$), $^{13}$C-NMR (CDCl$_3$): δ171.7, 171.3, 170.8, 170.6, 170.0, 169.7, 156.0, 134.9, 133.6, 128.4, 126.7, 123.4, 121.3, 116.9, 96.1, 69.4, 69.1, 68.9, 65.9, 62.1, 38.9, 38.6, 38.1, 26.2, 20.9, 20.7. Other chemical shifts are the same as for compound 26.

EXAMPLE 17

Synthesis of Compound 29

This example describes the synthesis of compound 29. Compound 29 was prepared from compound 4 and compound 19 using the peptide coupling protocol. Yield 70%; MS (positive FAB): 576 (MH$^+$), [α]$_D$: +70° C. (c, 1.1, CHCl$_3$), MP: 63.1~63.8° C., $^1$H-NMR (CDCl$_3$): δ7.89 (broad s, 1H, NH), 7.68 (d, 1H, J$_{tans}$=15.4 Hz, C(O)NH—CH=), 7.55 (d, 2H, J$_{om}$=8.3 Hz, aromatic-ortho), 7.40 (dd, 1H, J=3.0 Hz, $^4$J=4.9 Hz, thiophene), 7.28 (broad s, 1H, thiophene), 7.20 (broad d, 1H, thiophene), 7.00 (d, 2H, aromatic-meta), 6.40 (1H, d, =CH-thiophene), 5.53 (dd, 1H, J$_{23}$=3.5 HZ, J$_{34}$=10.0 Hz, H-3), 5.41 (m, 2H, H-1, H-2), 5.34 (dd, 1H, J$_3$4=9.9 Hz, J$_{45}$23 1, H-4), 4.25 (dd, 1H, J$_{56a}$=5.1 Hz, J$_{6ab}$=12.0 Hz, H-6a), 4.09~4.02 (m, 2H, H-5, H-6b), 2.17, 2.03, 2.02, 2.01 (4 AcO), $^{13}$C-NMR (CDCl$_3$): δ175.1, 173.0, 170.6, 170.0, 169.8, 156.0, 137.7, 133.6, 135.7, 127.6, 126.9, 125.0, 121.4, 120.5, 117.1, 96.1, 69.4, 69.1, 68.9, 66.0, 62.1, 26.2, 20.9, 20.7. Other chemical shifts are the same as for compound 26.

EXAMPLE 18

Synthesis of Compound 32

This example describes the synthesis of compound 32. A couple of drops of DIPEA was added to a solution of 3-thiophenehydrazide (compound 30) (0.2 g, 1.42 mmol) and 2-iminothiolane hydrochloride (compound 31) (0.2 g, 1 equiv) in degassed MeOH (5 mL) saturated with N$_2$. The resulting solution was stirred at room temperature for 3 h. p-Acrylamidophenyl methyl (5-acetamido-4,7,8,9-terta-O-acetyl-3,5-dideoxy-D-glycero-α-D-galacto-2-nonulopyranoside) onate (compound 2) (0.45 g, 0.7 mmol) in degassed CHCl$_3$ (5 mL) was injected slowly and continued to reaction overnight at the same condition. Solvent was briefly evaporated and the residue was dissolved in CHCl$_3$ (20 mL), washed with saturated NaHCO$_3$ and water and then dried over Na$_2$SO$_4$. The solution was condensed and the residue was purified by silica gel column chromatography (CHCl$_3$/MeOH, 10/1) to give a dark violet solid in 51% yield (0.33 g, 0.36 mmol). MS (positive FAB): 880.2 (M−Cl)$^+$, [α]$_D$: +10.0° (c, 3.6, CH$_3$OH), Mp: 103.5~104.7 C, $^1$H-NMR (CDCl$_3$): δ2.82 (broad t, 2H, HNC(O)—CH$_2$), 2.67 (broad t, 2H, CH$_2$—S), 2.53 (m, 4H, S—CH$_2$, CH$_2$—C(NH)), 1.85 (M, 2H, CH$_2$), $^{13}$C-NMR (CDCl$_3$): δ49.2, 36.5, 35.3, 30.5, 27.6. Other chemical shifts are the same as for compound 21.

EXAMPLE 19

Synthesis of Compound 33

This example describes the synthesis of compound 33. Compound 33 was prepared from compound 2 and compound 16 with iminothiolane hydrochloride (compound 31) using successive the ring opening and the peptide coupling protocol. Yield: 44%; MS (positive FAB): 922.3 (M−Cl)$^+$, $[\alpha]_D$: +1.4° (c, 1.4, MeOH), Mp: 115.2~116.7° C., $^1$H-NMR (CDCl$_3$): δ3.57 (s, 2H, CH$_2$-thiophene), 3.35 (broads, 4H, HN—CH$_2$CH$_2$—HNC(O)), 2.74 (NHC(O)—CH$_2$), 2.67 (broad s, 2H, CH$_2$—S), 2.52 (broad s, 2H, S—CH$_2$), 2.48 (broad s, 2H, CH$_2$C(NH)), 1.84 (M, 2H, CH$_2$), $^{13}$C-NMR (CDCl$_3$): δ42.7, 37.4, 37.1, 32.0, 31.4, 27.8, 27.1, 26.5. Other chemical shifts are the same as for compound 21.

EXAMPLE 20

Synthesis of Compound 34

This example describes the synthesis of compound 34. Compound 34 was prepared from compound 2 and compound 17 with iminothiolane hydrochloride (compound 31) using successive the ring opening and the peptide coupling protocol. Yield: 78%; MS (positive FAB): 1006.5 (M−Cl)$^+$, $[\alpha]_D$: +3.3° (c, 2.3, CHCl$_3$), Mp: 69.3~71.2° C., $^1$H-NMR (CDCl$_3$): 3.39~3.35 (m, 7H, CH$_2$-thiophene, CH$_2$—HNC (O), C(O)O—CH$_3$), 3.09 (m, 2H, C(NH)NH—CH$_2$), 2.86 (m, 6H, HNC(O)—CH$_2$CH$_2$SCH$_2$), 2.49 (m, 3H, H-3e, CH$_2$—C(NH)NH), 1.99 (m, 1H, H-3a), 1.86 (m, 2H, CH$_2$), 1.50 (m, 2H, CH$_2$), 1.34 (m, 2H, CH$_2$), 1.10~(m, 8H, 4 CH$_2$), $^{13}$C-NMR (CDCl$_3$): δ50.6, 42.5, 39.6, 37.9, 37.3, 30.7, 29.2, 28.8, 27.7, 27.5, 26.4. Other chemical shifts are the same as for compound 21.

EXAMPLE 21

Synthesis of Compound 35

This example describes the synthesis of compound 35. Compound 35 was prepared from compound 5 and 3-thiophenehydrazide (compound 30) with iminothiolane hydrochloride (compound 31) using successive steps of the ring opening and the peptide coupling protocols. Yield: 41%; MS (positive FAB): 737.0 (M−Cl)$^+$, $[\alpha]_D$: +30° (c, 1.2, CHCl$_3$), Mp: 69.7~70.4° C., $^1$H-NMR (CDCl$_3$): δ2.72 (broad t, 2H, HNC(O)—CH$_2$), 2.57 (broad t, 2H, CH$_2$—S), 2.43 (m, 4H, S—CH$_2$, CH$_2$—C(NH)), 1.80 (m, 2H, CH$_2$), $^{13}$C-NMR (CDCl$_3$): δ44.3, 37.1, 30.5, 27.4, 26.5. Other chemical shifts are the same as for compound 36.

EXAMPLE 22

Synthesis of Compound 36

This example describes the synthesis of compound 36. Compound 36 was prepared from compound 5 and compound 16 with iminothiolane hydrochloride (compound 31) using successive steps of the ring opening and the peptide coupling protocols. Yield 53%; MS (positive FAB,I: 779.4 (M−Cl)+, $[\alpha]_D$: +38.20° (c, 3.3, CHCl$_3$), Mp: 86.3~87.8° C., $^1$H-NMR (CDCl$_3$): δ9.50 (s, 1H, NH), 8.99 (s, 1H, NH), 8.75 (s, 1H, NH), 7.95 (s, 1H, NH), 7.53 (d, 2H, J=8.9 Hz, aromatic-ortho), 7.20 (broad d, 1H, thiophene), 7.07 (broad d, 1H, thiophene), 6.95, 6.92 (m, 3H, thiophene, aromatic-meta), 5.48 (dd, 1H, J$_{23}$=3.3 Hz, J$_{34}$=10.0 Hz, H-3), 5.42 (d, 1H, J$_{12}$=1.8 Hz, H-1), 5.39 (dd, 1H, H-2), 5.33 (dd, J$_{34}$=10.1 Hz, J$_{45}$≦1, H-4), 4.22 (dd, 1H, J$_{56a}$=4.7 Hz, J$_{6a6b}$=12.3 Hz, H-6a), 4.02 (m, 2H, H-5, H-6b), 3.51 (s, 2H, CH$_2$-thiophene), 3.38 (broad s, 4H, HN—CH$_2$CH$_2$—HNC(O)), 2.76 (NHC(O)—CH$_2$), 2.64 (broads, 2H, CH$_2$—S), 2.53 (broad s, 2H, S—CH$_2$), 2.44 (broad s, 2H, CH$_2$—C(NH)), 2.16, 2.02, 2.00, 1.99 (4 s, 12H, 4 AcO), 1.86 (m, 2H, CH$_2$), $^{13}$C-NMR (CDCl$_3$): δ175.6, 171.8, 170.7, 170.5, 170. 1, 169.7, 168.0, 152.0, 134.5, 133.7, 128.5, 126.2, 123.3, 121.6, 116.9, 96.1, 69.3, 69.1, 68.9, 65.9, 62.1, 42.8, 37.5, 37.3, 32.1, 31.4, 27.6, 27.1, 26.2, 20.9, 20.7. Other chemical shifts are the same as for compound 36.

EXAMPLE 23

Synthesis of Compound 37

This example describes the synthesis of compound 37. Compound 37 was prepared from compound 5 and compound 17 with iminothiolane hydrochloride (compound 31) using successive steps of the ring opening and the peptide coupling protocols. Yield: 43%; MS (positive FAB): 863.5 (M−Cl)$^+$, $[\alpha]_D$: +25.0° (c, 1.6, CHCl$_3$), Mp: 69.3~71.2° C., $^1$H-NMR (CDCl$_3$): δ3.19 (m, 2H, CH$_2$—HNC(O)), 3.07 (m, 2H, C(NH)NH—CH$_2$), 2.12, 1.98, 1.96 (3 s, 12H, AcO), 1.84 (m, 2H, CH$_2$), 1.50 (m, 2H, CH$_2$), 1.34 (m, 2H, CH$_2$), 1.15 (m, 8H, 4 CH$_2$), $^{13}$C-NMR (CDCl$_3$): δ50.6, 42.9, 39.6, 37.8, 37.3, 30.7, 29.2, 28.7, 27.6, 27.5, 26.4. Other chemical shifts are the same as for compound 36.

EXAMPLE 24

Synthesis of Compound 38

This example describes the synthesis of compound 38. Compound 38 was prepared from compound 5 and compound 20 with iminothiolane hydrochloride (compound 31) using successive steps of the ring opening and the peptide coupling protocols. Yield: 35%; MS (positive FAB): 875.5 (M−Cl)$^+$, $[\alpha]_D$: +39.2° (c, 2.2, CHCl$_3$), Mp: 88.7~90.0° C., $^1$H-NMR (CDCl$_3$): δ7.45 (d, 1H, J$_{trans}$=15.4 Hz, HNC(O)—CH=), 6.48 (d, 1H, =CH-thiophene), 3.25 (m, 4H, CH$_2$—HNC(O), 3.07 (C(NH)NH—CH$_2$), 2.15, 2.01, 2.00, 1.99 (4 s, 12H, AcO), 1.85 (m, 2H, CH$_2$), 1.54 (m, 2H, CH$_2$), 1.42 (m, 2H, CH$_2$), 1.23~1.14 (m, 8H, 4 CH$_2$), $^{13}$C-NMR (CDCl$_3$): δ137.8, 121.6, 50.6 42.9, 39.8, 37.3, 37.3, 30.7, 29.27 28.8, 27.6, 27.5, 26.4. Other chemical shifts are the same as for compound 36.

EXAMPLE 25

Synthesis of Poly[methyl (3-thienyl)acetate] (Compound 39)

This example describes the synthesis of poly[methyl (3-thienyl)acetate] (compound 39). Compound 7 (4.9 g, 34.4 mmol) in dry CHCl$_3$ (20 mL) was slowly added (over a 5 h period) to a solution of FeCl$_3$ (22.4 g, 0.1 mol) in dry CHCl$_3$ (50 mL) saturated by N$_2$ gas. The resulting emulsion was stirred for 3 days under N$_2$ atmosphere at an ambient temperature. MeOH was directly added to a reaction flask to induce precipitate and stirred another couple of hours. A dark brown solid was filtered briefly washed with MeOH. The polymer was then washed by Soxhlet extraction using MeOH and then dried under reduced pressure to give dark-brownish solid (3.3 g) in 67% (w/w) yield. $^1$C-NMR (CDCl$_3$): δ7.20 (broad t, 1H, thiophene), 3.75~3.61 (m, 5H, CH$_2$, CH$_3$).

EXAMPLE 26

Synthesis of Poly(thiopheneacetic acid) (Compound 40)

This example describes the synthesis of poly (thiopheneacetic acid) (compound 40). NaOH (85 mg, 1.2 equiv) was added to a solution of poly(thiophenemethyl ester) (compound 39) (0.3 g) in MeOH (20 mL). The mixture was refluxed overnight. The resulting dark red homogeneous solution was cooled down to ice water temperature and acidified by concentrated HCl. The precipitate was filtered, successively washed with distilled water and dried under reduced pressure to give light brown solid (0.27 g) in 90% (w/w) yield.

EXAMPLE 27

Synthesis of Poly(thiophene-spacer-sialic acid-co-thiopheneacetic acid) (Compound 41)

This example describes the synthesis of poly(thiophene-spacer-sialic acid-co-thiopheneacetic acid) (compound 41). TBTU (30 mg, 1.2 eq.) and DIPEA (3 drops) was added to a solution of poly(thiopheneacetic acid) (compound 40) (50 mg, 76 $\mu$mol) (3 mL) and compound 3 (54.3 mg, 1 eq.) in DMF. The resulting solution was stirred at an ambient temperature for 5 h. Once complete consumption of sialic acid derivative, the solution was condensed to the volume of one-third and then added MEOH (10 mL). The solution was allowed to stand in the refrigerator for 1 day to induce precipitation. A brown solid was filtered and then washed successively with MEOH and dried under reduced pressure to give the desired product (50 mg) in 49% (w/w) yield.

EXAMPLE 28

Bioassays of Glyco-PTs with Proteins

This example describes colorimetric assays using glyco-PTs and protein ligands. The biochromic capability of glyco-PTs was evaluated with various proteins such as lectins, virus, and bacteria depending on carbohydrate ligands. It was found that 15–20 $\mu$L of protein stock solution was optimal, producing a detectable color change within 4–5 h. To maximize color change, incubation times were allowed up to 12 h. However, longer incubation times resulted in precipitation of the glyco-PT-protein complexes.

EXAMPLE 29

Precipitation Assays with Lectins (ConA and WGA)

This example describes precipitation assays using the glycopolymers and lectins. A glycopolymer stock solution was diluted 1:4–5 in 0.01 M phosphate buffer (pH=7.3). 300 $\mu$L of this solution was transferred to a 500 $\mu$L eppendorf tube. A total of 20 $\mu$L of stock solution prepared from lectin (1 mg/mL, 0.01 M PBS) was mixed and incubated at room temperature for 12 h. Visible absorption spectra were recorded and compared with the same concentration of the mother solution as a negative control. Each test was performed in duplicate.

EXAMPLE 30

Precipitation Assays with Concanavalin A-Biotin-Streptavidin

This example describes precipitation assays using glyco-polymers and Concanavalin A-Biotin-Streptavidin ligands. A glycopolymer stock solution was diluted 1:4–5 in 0.01 M phosphate buffer (pH=7.3). Two 300 $\mu$L portions of the solution were transferred to two 500 $\mu$L eppendorf tubes. Into each of these tubes 20 $\mu$L of stock solution prepared from biotin labelled Con A (1 mg/mL, 0.01 PBS) was mixed and preincubated at room temperature for 1 h. Subsequently 20 $\mu$L of Streptavidin (1 mg/mL, 0.01 M PBS) was added and incubated at room temperature for 10–12 h. Visible absorption spectra were recorded and compared with the same concentration of the mother solution as a negative control. A precipitate was detected visually within the first 4–5 h after addition of the streptavidin. Each test was performed in duplicate.

EXAMPLE 31

Colorimetric Assay with *E. coli,* Strain HB101

This example describes an assay using glycopolymers and bacterial protein ligands. *E. coli* strain HB101 (pSH2) were grown for 24 h in static LB broth and the solution was gently centrifuged and collected a clear supernatant before use. A glycopolymer stock solution was diluted 1:4~5 in 0.01 M phosphate buffer (pH=7.3) and 300 $\mu$L of the solution was transferred to a 500 $\mu$L eppendorf tube. After centrifugation of the stock solution, 20 $\mu$L of supernatant *E. coli* HB101 was mixed and incubated at room temperature for 12 h. The visible absorption spectra were recorded and compared with the same concentration of the mother solution as a negative control. The darker red color of *E. coli* treated mannose-PTs was verified visually with the brownish colored mother solution. Each test was performed in duplicate.

EXAMPLE 32

Colorimetric Assays with Influenza Virus A/B

This example describes an assay using glycopolymers and viral ligands. A glycopolymer stock solution was diluted 1:4–5 in 0.01 M phosphate buffer (pH=7.3) and 300 $\mu$L of the solution was transferred to a 500 $\mu$L eppendorf tube. To this tube, 20 $\mu$L of stock solution of Influenza Virus A or B was mixed and incubated at 4° C. for 2–12 h. The visible absorption spectrum was recorded and compared with the same concentration of the mother solution as a negative control. The darker red color of Influenza virus-treated sialic acid-PTs was verified visually with the brownish colored mother solution. Each test was performed in duplicate.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in material science, chemistry, and molecular biology or related fields are intended to be within the scope of the following claims.

We claim:

1. A biopolymeric composition comprising:
   a plurality of polymer molecules,
   a plurality of spacer molecules, and
   one or more ligands,
wherein said plurality of polymer molecules are selected from the group consisting of polythiophene, and glycopolythiophene, and wherein said plurality of spacer molecules join said plurality of polymer molecules to said one or more ligands, and wherein said biopolymeric composition undergoes a color change upon the binding of an analyte to said one or more ligands.

2. The biopolymeric composition of claim 1, wherein one or more members of said plurality of spacer molecules are hydrophobic.

3. The biopolymeric composition of claim 1, wherein one or more members of said plurality of spacer molecules are hydrophilic.

4. The biopolymeric composition of claim 1, wherein said one or more ligands are linked to one or more members of said plurality of polymer molecules through one or more of said plurality of spacer molecules via covalent bonds.

5. The biopolymeric composition of claim 4, wherein said covalent bonds are selected from the group consisting of amine bonds, thiol bonds, aldehyde bonds, glycosidic bonds, and peptide bonds.

6. The biopolymeric composition of claim 1, further comprising a dopant material.

7. The biopolymeric composition of claim 6, wherein said dopant material is selected from the group consisting of surfactants, polysorbate, octoxynol, sodium dodecyl sulfate, polyethylene glycol, zwitterionic detergents, decylglucoside, deoxycholate, diacetylene derivatives, phosphatidylserine, phosphatidylinositol, phosphatidylethanolamine, phosphatidylcholine, phosphatidylglycerol, phosphatidic acid, phosphatidylmethanol, cardiolipin, ceramide, cholesterol, steroids, cerebroside, lysophosphatidylcholine, D-erythroshingosine, sphingomyelin, dodecyl phosphocholine, and N-biotinyl phosphatidylethanolamine.

8. The biopolymeric composition of claim 1, wherein said one or more ligands further comprise one or more protein ligands.

9. The biopolymeric composition of claim 8, wherein said one or more protein ligands further comprise antibodies or portions of antibodies.

10. The biopolymeric composition of claim 1, wherein said one or more ligands further comprise one or more non-protein ligands.

11. The biopolymeric composition of claim 10, wherein said one or more non-protein ligands are selected from the group consisting of carbohydrates, nucleic acids, drugs, chromophores, antigens, chelating compounds, molecular recognition complexes, ionic groups, polymerizable groups, linker groups, electron donors, electron acceptor groups, hydrophobic groups, hydrophilic groups, receptor binding groups, trisaccharides, tetrasaccharides, ganglioside $G_{M1}$, ganglioside $G_{T1b}$, sialic acid, and combinations thereof.

12. The biopolymeric composition of claim 1, wherein said analyte is selected from the group consisting of pathogens, drugs, receptor ligands, antigens, ions, hormones, blood components, disease indicators, cell components, antibodies, lectins, enzymes, organic solvents, volatile organic compounds, pollutants, and genetic material.

13. The biopolymeric composition of claim 12, wherein said analyte is a pathogen selected from the group consisting of viruses, bacteria, parasites, and fungi.

14. The biopolymeric composition of claim 13, wherein said virus is selected from the group consisting of influenza, rubella, varicella-zoster, hepatitis A, hepatitis B, herpes simplex, polio, small pox, human immunodeficiency virus, vaccinia, rabies, Epstein Barr, reoviruses, and rhinoviruses.

15. The biopolymeric composition of claim 13, wherein said pathogen is a bacterium selected from the group consisting of *E. coli, Mycobacterium tuberculosis,* Salmonella, Chlamydia and Streptococcus.

16. The biopolymeric composition of claim 13, wherein said pathogen is a parasite selected from the group consisting of Plasmodium, Trypanosoma, *Toxoplasma gondii,* and Onchocerca.

17. A method of detecting the presence of an analyte, comprising:
 a) providing:
  i) a plurality of polymer molecules, wherein said plurality of polymer molecules are selected from the group consisting of polythiophene, and glycopolythiophene;
  ii) a plurality of spacer molecules;
  iii) one or more ligands; and
  iv) a sample suspected of containing an analyte;
 b) contacting said plurality of biopolymeric molecules with said sample; and
 c) detecting a color change in said plurality of biopolymeric molecules caused by the binding of said analyte to said one or more ligands.

* * * * *